US010492702B2

United States Patent
Chang et al.

(10) Patent No.: US 10,492,702 B2
(45) Date of Patent: Dec. 3, 2019

(54) REAL-TIME CORTICAL MAPPING

(71) Applicant: The Regents of the University of California, Oakland, CA (US)

(72) Inventors: Edward Chang, San Francisco, CA (US); Connie Cheung, San Jose, CA (US)

(73) Assignee: The Regents of the University of California, Oakland, CA (US)

( * ) Notice: Subject to any disclaimer, the term of this patent is extended or adjusted under 35 U.S.C. 154(b) by 1158 days.

(21) Appl. No.: 14/375,099

(22) PCT Filed: Jan. 30, 2013

(86) PCT No.: PCT/US2013/023851
§ 371 (c)(1),
(2) Date: Jul. 28, 2014

(87) PCT Pub. No.: WO2013/116341
PCT Pub. Date: Aug. 8, 2013

(65) Prior Publication Data
US 2015/0313497 A1    Nov. 5, 2015

Related U.S. Application Data

(60) Provisional application No. 61/592,782, filed on Jan. 31, 2012.

(51) Int. Cl.
*A61B 5/04*    (2006.01)
*A61B 5/0476*    (2006.01)
*A61B 5/0484*    (2006.01)
*A61B 5/00*    (2006.01)
(Continued)

(52) U.S. Cl.
CPC ...... *A61B 5/04012* (2013.01); *A61B 5/04001* (2013.01); *A61B 5/048* (2013.01); *A61B 5/0484* (2013.01); *A61B 5/4094* (2013.01); *A61B 5/742* (2013.01); *A61B 5/4848* (2013.01); *A61B 5/743* (2013.01); *A61B 2562/046* (2013.01); *A61N 1/0531* (2013.01)

(58) Field of Classification Search
USPC ................................................. 600/544, 545
See application file for complete search history.

(56) References Cited

U.S. PATENT DOCUMENTS

| 4,084,583 A | 4/1978 | Hjort |
| 5,119,816 A | 6/1992 | Gevins |
| 5,291,888 A | 3/1994 | Tucker |

(Continued)

OTHER PUBLICATIONS

Miller et al. Real-time functional brain mapping using electrocorticography. NeuroImage 37 (2007) 504-507.*

(Continued)

*Primary Examiner* — Etsub D Berhanu
(74) *Attorney, Agent, or Firm* — Edward J. Baba; Shweta H. Chandra; Bozicevic, Field & Francis LLP

(57) ABSTRACT

Methods of cortical mapping in real-time are provided. Aspects of the methods include performing real-time processing of signals indicative of a subject's brain activity by applying one filter or more to the signals, wherein the processing is in the absence of averaging based on time. Systems for cortical mapping in real-time are also provided. The methods and systems are useful in research, diagnostic, and therapeutic applications.

31 Claims, 13 Drawing Sheets

(A)

(B)

(51) Int. Cl.
*A61B 5/048* (2006.01)
*A61N 1/05* (2006.01)

(56) References Cited

U.S. PATENT DOCUMENTS

| | | | |
|---|---|---|---|
| 5,361,773 | A | 11/1994 | Ives |
| 5,479,934 | A | 1/1996 | Imran |
| 5,724,984 | A | 3/1998 | Arnold et al. |
| 5,817,029 | A | 10/1998 | Gevins et al. |
| 6,256,531 | B1 | 7/2001 | Ilmoniemi et al. |
| 6,381,481 | B1 | 4/2002 | Levendowski et al. |
| 6,510,340 | B1 | 1/2003 | Jordan |
| 7,239,910 | B2 | 7/2007 | Tanner |
| D565,735 | S | 4/2008 | Washbon |
| D603,051 | S | 10/2009 | Causevic et al. |
| 7,715,607 | B2 | 5/2010 | Hu et al. |
| 7,908,009 | B2 | 3/2011 | Wyler et al. |
| D641,886 | S | 7/2011 | Causevic et al. |
| 8,019,142 | B2 | 9/2011 | Nowinski et al. |
| D647,208 | S | 10/2011 | Rothman et al. |
| 8,045,775 | B2 | 10/2011 | Volkau et al. |
| 2005/0182456 | A1 | 8/2005 | Ziobro et al. |
| 2006/0129056 | A1 | 6/2006 | Leuthardt et al. |
| 2007/0161919 | A1* | 7/2007 | DiLorenzo ......... A61B 5/04001 600/544 |
| 2007/0162080 | A1* | 7/2007 | Brockway ............ A61B 5/0538 607/17 |
| 2007/0179534 | A1 | 8/2007 | Firlik et al. |
| 2009/0062680 | A1* | 3/2009 | Sandford ........... A61B 5/04012 600/544 |
| 2011/0130675 | A1 | 6/2011 | Bibian et al. |
| 2012/0021394 | A1 | 2/2012 | Decharms |

OTHER PUBLICATIONS

Ajmone-Marsan, "Electrocorticography: Historical Comments on its Development and the Evolution of its Practical Applications" Electroencephalogr Clin Neurophysiol Suppl (1998) 48:9-16.

Canolty et al., "High Gamma Power is Phase-Locked to Theta Oscillations in Human Neocortex" Science (2006) 313(5793):1626-1628.

Chang et al., "Cortical Spatio-temporal Dynamics Underlying Phonological Target Detection in Himans" Journal of Cognitive Neuroscience (2011) 23(6):1437-1446.

* cited by examiner

REAL-TIME CORTICAL MAPPING

CROSS-REFERENCE TO RELATED APPLICATION

Pursuant to 35 U.S.C. § 119 (e), this application claims priority to the filing date of the U.S. Provisional Patent Application Ser. No. 61/592,782, filed Jan. 31, 2012; the disclosure of which is incorporated herein by reference.

STATEMENT REGARDING FEDERALLY SPONSORED RESEARCH

This invention was made with government support under Grant No. NS065120 awarded by the National Institutes of Health. The government has certain rights in the invention.

BACKGROUND

Cortical mapping is a useful tool in carrying out neurosurgical procedures near "eloquent" brain regions. Such neurosurgical procedures may be performed in a subject suffering from one of a number of diseases. For example, nearly 50 million people worldwide suffer from epilepsy, a chronic neurological disorder. Epilepsy is often successfully treated using medications. However, in a large percentage of cases sufferers do not have control of their seizures. In many cases, surgery to remove the epileptic focus is necessary. Surgical procedures may produce trauma to the patient and run the risk of removing brain areas that are critical to language, sensorimotor, or cognitive function, often resulting in some degree of neurological impairment the patient. As a result, clinicians must map the functionality of the brain tissue prior to resection to ensure that the removal of critical tissue is minimal.

The traditional method for cortical mapping is electrical cortical stimulation (ECS). Using ECS, only one site can be tested at a given time and must often be tested repetitively for confirmation. It may evoke unwanted seizures. And, ECS can misrepresent important information about distributed cortical operations. As a result, patients often have neurologic impairments after surgery despite comprehensive ECS mapping.

SUMMARY

Methods of cortical mapping in real-time are provided. Aspects of the methods include performing real-time processing of input signals by applying one filter or more to the input signals, wherein the processing is in the absence of averaging based on time. Systems for cortical mapping in real-time are also provided. The provided methods and systems are useful in research, diagnostic, and therapeutic applications including carrying out neurosurgical procedures on a subject.

Methods of the present disclosure include cortical mapping in real time, the methods including positioning electrodes to detect a subject's brain activity; receiving a plurality of signals from the electrodes; processing the signals in real-time by applying a filter to the plurality of input signals, wherein the processing is in the absence of averaging based on time so as to provide separation of time-dependent activation signals in sensory and motor cortices of the subject's brain; and communicating the processed input signals to an output device.

As such, aspects of methods of the present disclosure do not discard temporal information that could facilitate the understanding of important dynamics, such as latency differences between activation in sensory, motor and cognitive processes; such dynamical differences may provide insight into differing cortical functionality (e.g. motor versus somatosensory), which may facilitate surgical planning decisions that, e.g., minimize morbidity. The methods may provide a substantially continuous real-time indication of the subject's brain activity. Subjects suitable for cortical mapping via methods disclosed herein include mammals, e.g., humans.

In some instances, a plurality of electrodes is positioned to detect a subject's brain activity. The precise number of electrodes may vary, ranging in some instances from 1 to 256 or more, including, e.g., 36, 64, 81, 100, 144, 169, 196, 225, or 256 electrodes.

Processing of input signals may vary. In some instances, processing is in the absence of averaging based on time so as to provide adequate separation so as to detect between activation signals in sensory and motor cortices of the subject's brain. Processing may include one or more filters. Filters employed in various embodiments of the described methods include notch, bandpass, and/or low-pass filters. The frequency at which a notch filter may be applied may vary, ranging in some instances to a frequency between 50 Hz to 240 Hz, such as 60 Hz, 120 Hz, or 180 Hz. A bandpass filter may separate a signal in 2 to 8 or more different frequency bands, including 4 to 7 frequency bands, e.g., seven frequency bands. In some instances, a low-pass filter may be applied to an input signal directly, while in others it may also, or instead, be applied to an absolute value of a signal.

In certain instances, the method includes approximating an envelope of an input signal. Approximating an envelope of an input signal may be achieved by any convenient means, including without limitation applying a Hilbert transform to the signal; a Fourier transform to the signal; or a low-pass filter to an absolute value of the signal. Processing may include calculating the phase of a signal. Calculating the phase of a signal may include calculation using a Hilbert transform.

In certain embodiments, the signals are electrocorticographic (ECoG) signals. The ECoG signals may be sampled from a subject using intracranial electrodes. The intracranial electrodes may be implanted between a subject's scalp and skull. The electrodes may be arranged in any convenient pattern, including in a grid pattern, wherein the grid spacing is 0.1 to 1.5 cm, or more. Aspects also include electrodes arranged in no pattern or in irregular patterns. Electrodes may be microelectrodes.

In certain embodiments, input signals include frequencies of 4 to 500 Hz. Input signals may include mu, beta, gamma, or high gamma frequencies.

In certain embodiments, certain steps of a method are updated or repeated every 1 second or less. The steps may be updated or repeated every 0.5 seconds or less. The steps may be updated or repeated every 0.15 seconds or less. In certain embodiments, a subject is directed to perform a task. Certain steps may be repeated continuously while a subject performs a task.

In another aspect, a method is provided that includes positioning a plurality of ECoG electrodes to detect a subject's brain activity; collecting a plurality of signals from the plurality of ECoG electrodes; processing each signal by applying a filter to create a filtered signal and approximating an envelope of the filtered signal, wherein the processing is in the absence of averaging based on time so as to provide separation of activation signals in sensory and motor cortices of the subject's brain; and communicating the processed signals to an output device. At any time during this method, the subject may perform a task and/or be directed to perform a task. Such a task may be a motor task. In some embodiments, the steps of collecting a plurality of signals, processing each signal, and communicating the processed signals to an output device are performed continuously while the subject performs a task.

In another embodiment, a method is provided that includes positioning a plurality of electrodes to detect a subject's brain activity; receiving a first plurality of input signals indicative of a subject's brain activity; performing real-time processing of the first plurality of input signals by applying a filter to the plurality of input signals, wherein the processing is in the absence of averaging based on time so as to provide separation of activation signals in sensory and motor cortices of the subject's brain; administering an agent to the subject; receiving a second plurality of input signals indicative of the subject's brain activity; performing real-time processing of the second plurality of input signals by applying a filter to the second plurality of input signals, wherein the processing is in the absence of averaging based on time so as to provide separation of activation signals in sensory and motor cortices of the subject's brain; and identifying physiological information concerning the subject based upon differences between the first plurality of signals and the second plurality of signals.

The present disclosure also provides systems for cortical mapping. In one embodiment, a system includes a plurality of electrodes; a processor; and a machine-readable medium encoding instructions operable to cause the processor to perform real-time operations including: obtaining, from the plurality of electrodes, a plurality of brain signals of a subject; processing each the sensed brain signal by applying a filter to the brain signal, wherein the processing is in the absence of averaging based on time so as to provide separation of activation signals in sensory and motor cortices of the subject's brain; and identifying physiological information concerning the subject based on the plurality of processed sensed brain signals. The electrodes of the system may be intracranial electrodes.

These and other features will be apparent to the ordinarily skilled artisan upon reviewing the present disclosure.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1:
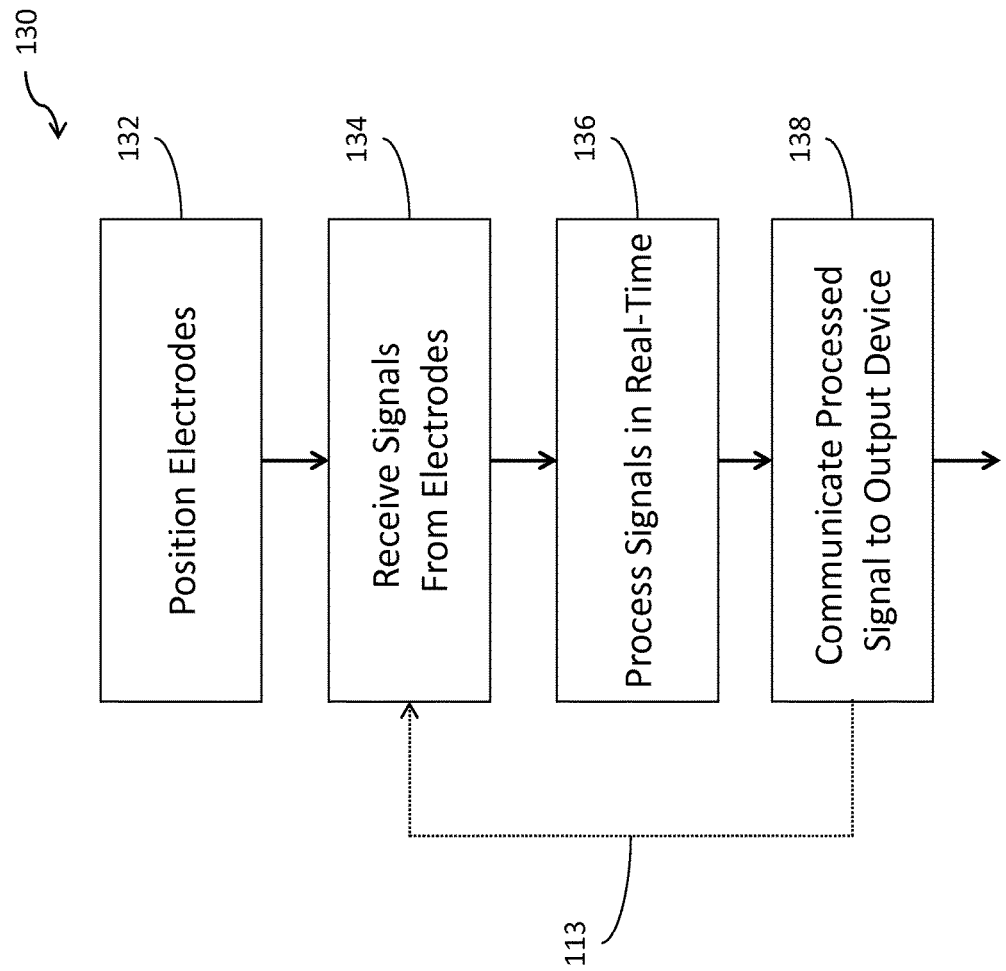
FIG. 1 depicts a flowchart of one embodiment of a method of the instant disclosure.

Methods of cortical mapping in real-time are provided. Aspects of the methods include performing real-time processing of input signals by applying one filter or more to the input signals, wherein the processing is in the absence of averaging based on time. Systems for cortical mapping in real-time are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode" includes a plurality of such electrodes and reference to "the signal" includes reference to one or more signals, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include methods of cortical mapping of a subject in real time. The terms phrases "cortical mapping" and "cortical map" are used broadly and generically to refer to methods or processes useful for understanding the functional organization of a subject's cortical areas. The phrases are meant to specifically include methods that can extract event-related neural activity to localize important cortical brain regions, non-limiting examples of which are sensory and motor cortices.

A feature of aspects of the invention is that cortical mapping of a subject is in real-time. The phrase "real-time" is broadly used herein to signify that a method includes online analyses, with results available without significant delay, e.g., within 10 seconds or less, 5 seconds or less, or 1 second or less. Examples of methods that do not constitute "real-time" cortical mapping include those consisting of offline analyses.

Such real-time cortical mapping methods of the invention are suitable for application to a variety of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). The subject methods may be applied to human subjects of both genders and at any stage of development (i.e., neonates, infant, juvenile, adolescent, adult), where in certain embodiments the human subject is a juvenile, adolescent or adult. While the present invention may be applied to a human subject, it is to be understood that the subject methods may also be carried-out on other animal subjects such as, but not limited to, birds, mice, rats, dogs, cats, livestock and horses.

In certain embodiments, the subject methods may include a diagnostic step. Individuals may be diagnosed as being in need of the subject methods using any convenient protocol. Moreover, suitable subjects of this invention include those who have and those who have not previously been afflicted with seizures, those that have previously been determined to be at risk of suffering from seizures, and those who have been initially diagnosed or identified as being afflicted with or experiencing seizures. In some instances, the subject may be suffering from a condition for which cortical mapping may be desired, such as epilepsy or brain tumors. Suitable subjects of this invention may also include those who have undergone or will undergo a craniotomy or other type of brain surgery.

FIG. 1 is a flowchart of one aspect of a method of the instant disclosure. In the embodiment 100 illustrated in FIG. 1, electrodes are positioned 102 to detect a subject's brain activity. The signal from these electrodes is received 104 and processed by applying one filter or more 106, wherein the processing is in the absence of averaging based on time. The processed signal is then communicated to an output device 108. The steps labeled 104 to 108 may be repeated 110. While steps 104 to 108 are repeated, the subject may perform a task, be directed to perform a task, and/or experience an involuntary event (e.g., a seizure, such as a naturally occurring seizure, a seizure induced or caused by an external stimulus, etc.). The method 100 is able to produce a cortical mapping of the subject in real-time, with the resolution of the cortical map determined by a number of factors including, but not limited to, factors such as the number of electrodes positioned, the type of electrodes, the location of the electrodes, the spacing of the electrodes, the specific processing steps employed, the filter(s) employed, the task performed (if any), and the like.

As one of skill in the relevant art would find apparent from the following description, the configuration illustrated in FIG. 1 is just one example of the present disclosure. Many other embodiments and variations are contemplated, many of which are described in greater detail below.

Positioning of Electrodes

In practicing methods of the invention, a subject's brain activity is detected, by any convenient means. In many instances, detecting a subject's brain activity includes positioning one or more electrodes, wherein the electrode(s) are of a suitable type and position so as to detect a subject's brain activity.

For example, a subject's brain may first be imaged by any convenient means, such as magnetic resonance imaging (MRI). Electrodes may be positioned so as to correspond to particular landmarks or regions in the subject's brain. In certain aspects, correct placement of electrodes may be confirmed by any convenient means, including visual inspection or computed tomography (CT) scan. In some aspects, after electrode positions are confirmed they may be superimposed on a surface reconstruction image of the subject's brain. A non-limiting example of such a superimposition is provided in FIG. 2, in which a subject undergoing a method as provided herein had 64 electrodes positioned, with the electrode positions extracted by CT scan, co-registered with the patient's MRI, and then superimposed on the subject's 3D MRI surface reconstruction image.

The specific location at which to position an electrode may be determined by identification of anatomical landmarks in a subject's brain, such as the pre-central and post-central gyri and the central sulcus. Identification of anatomical landmarks in a subject's brain may be accomplished by any convenient means, such as magnetic resonance imaging (MRI), functional magnetic resonance imaging (fMRI), and visual inspection of a subject's brain while undergoing a craniotomy. Once a suitable location for an electrode is determined, the electrode may be positioned or implanted according to any convenient means.

Methods of interest for positioning electrodes include, but are not limited to, those described in U.S. Pat. Nos. 4,084,583; 5,119,816; 5,291,888; 5,361,773; 5,479,934; 5,724,984; 5,817,029; 6,256,531; 6,381,481; 6,510,340; 7,239,910; 7,715,607; 7,908,009; 8,045,775; and 8,019,142; the disclosures of which are incorporated herein by reference.

Though in some embodiments one electrode may positioned, in many embodiments more than one electrode may be positioned. More than one electrode may be employed so as to provide greater resolution in the cortical mapping, as each electrode may convey information about the activity of a particular region. By comparing differences between the signals of each electrode, a cortical map may be created. Accordingly, in certain embodiments, between about 5 and 256 electrodes, or more, may be employed. In some embodiments, the number of electrodes positioned is about 5 to 10 electrodes, about 10 to 20, about 20 to 30, about 30 to 40, about 40 to 50, about 60 to 70, about 70 to 80, about 80 to 90, about 90 to 100, about 100 to 110, about 110 to 120, about 120 to 130, about 130 to 140, about 140 to 150, about 150 to 160, about 160 to 170, about 170 to 180, about 180 to 190, about 190 to 200, about 200 to 210, about 210 to 220, about 220 to 230, about 230 to 240, or about 240 to 256 or more. When more than one electrode is employed, the electrodes may be homogeneous or heterogeneous.

Figure 2:
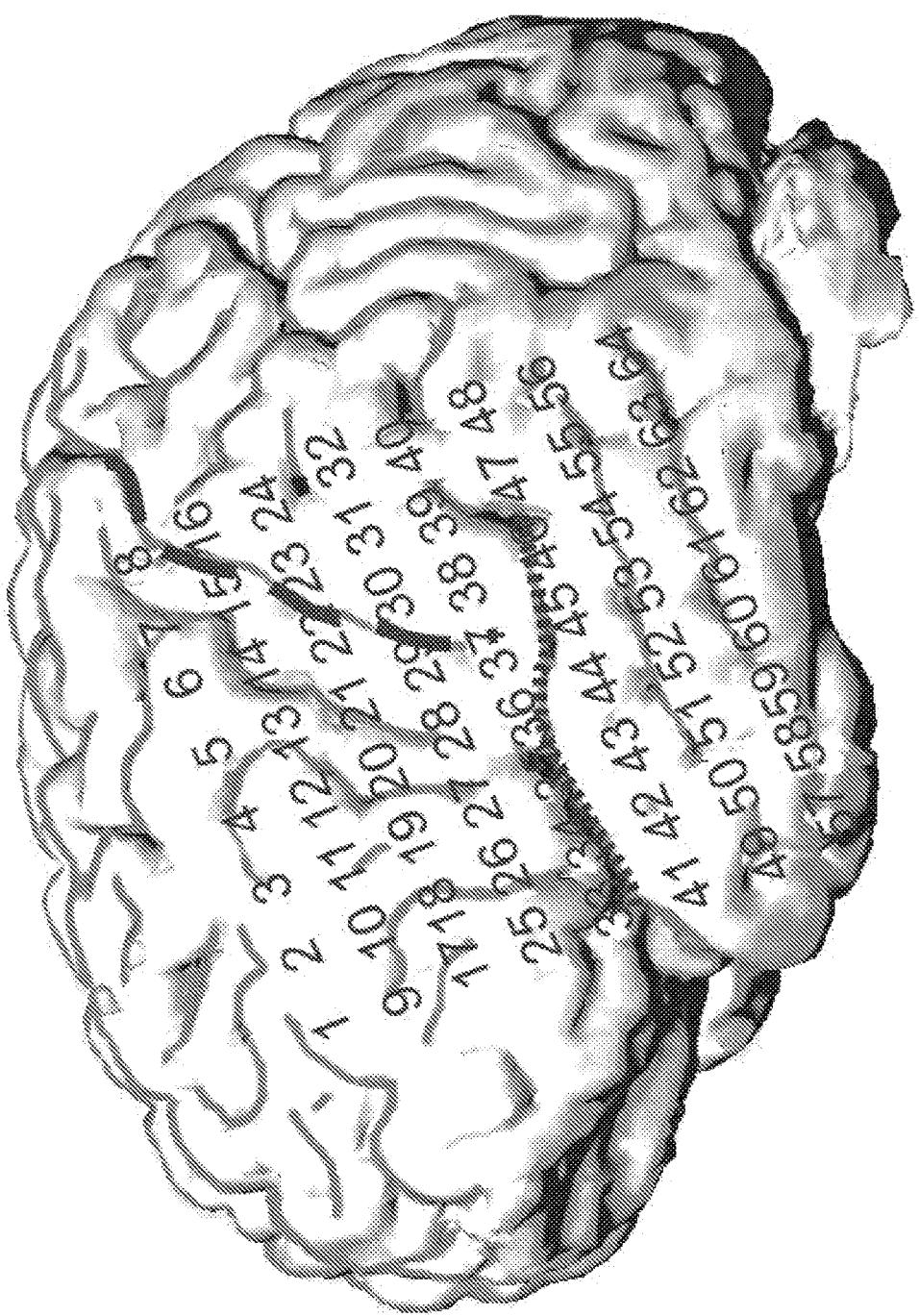
FIG. 2 depicts a possible arrangement of electrodes to detect a subject's brain activity. A 64-channel subdural ECoG electrode array implanted over Subject A's left lateral hemisphere is shown. Electrode numbers are superimposed on the 3D MR surface reconstruction image. The central sulcus and Sylvian fissure are outlined with dashed and dotted lines, respectively.

FIG. 2 illustrates one manner in which a plurality of electrodes may be positioned in accordance with the instant disclosure. In the embodiment illustrated in FIG. 2, a 64-channel subdural ECoG electrode array was implanted over the left lateral hemisphere of a subject's brain. Electrode numbers are superimposed on the 3D MR surface reconstruction image of the subject's brain.

As is apparent from FIG. 2, electrodes may be arranged in no particular pattern or any convenient pattern to facilitate cortical mapping. For example, a plurality of electrodes may be placed in a grid pattern, in which the spacing between adjacent electrodes is approximately equivalent. Such spacing between adjacent electrodes may be, for example, about 2.5 cm or less, about 2 cm or less, about 1.5 cm or less, about 1 cm or less, about 0.5 cm or less, about 0.1 cm or less, or about 0.05 cm or less. The spacing between electrodes may be selected so as to determine the level of resolution of the cortical mapping, with smaller spacing chosen to provide higher resolution mapping, or vice versa. Electrodes placed in a grid pattern may be arranged such that the overall plurality of electrodes forms a roughly geometrical shape. In certain embodiments, a grid pattern may be roughly square in overall shape, roughly rectangular, or roughly trapezoidal.

Electrodes may also be pre-arranged into an array, such that the array includes a plurality of electrodes that may be placed on or in a subject's brain. Such arrays may be miniature- or micro-arrays, a non-limiting example of which may be a miniature ECoG array. An array may include, for example, about 200 electrodes or less, about 100 electrodes or less, about 90 electrodes or less, about 80 electrodes or less, about 70 electrodes or less, about 60 electrodes or less, about 50 electrodes or less, about 40 electrodes or less, about 30 electrodes or less, about 20 electrodes or less, or about 10 electrodes or less. In certain embodiments, the array may cover a surface area of about 1 $cm^2$, about 1 to 10 $cm^2$, about 10 to 25 $cm^2$, about 25 to 50 $cm^2$, about 50 to 75 $cm^2$, about 75 to 100 $cm^2$, or 100 $cm^2$ or more. Arrays of interest may include, but are not limited to, those described in U.S. Pat. No. D565,735; U.S. Pat. No. D603,051; U.S. Pat. No. D641,886; and U.S. Pat. No. D647,208; the disclosures of which are incorporated herein by reference.

Electrodes may be platinum-iridium electrodes or be made out of any convenient material. The diameter, length, and composition of the electrodes to be employed may be determined in accordance with routine procedures known to those skilled in the art. Factors which may be weighted when selecting an appropriate electrode type may include but not be limited to the desired location for placement, the type of subject, the age of the subject, cost, duration for which the electrode may need to be positioned, and other factors.

In certain embodiments, the electrodes may be intracranial electrodes. Such electrodes may be implanted between a subject's scalp and a subject's skull. Intracranial electrodes may be positioned and arranged as described previously.

In some embodiments, the electrodes may be ECoG electrodes or may include an ECoG array. The ECoG electrodes may be intracranial, and may be implanted between a subject's scalp and a subject's skull. For a general review of ECoG technology, see Among-Marsan, C. Electrocorticography: Historical Comments on its Development and the Evolution of its Practical Applications, *Electroencephalogr. Clin. Neurophysiol, Suppl.* 1998, 48: 10-16; the disclosure of which is incorporated herein by reference.

In certain embodiments, a ground electrode or reference electrode may be positioned. A ground or reference electrode may be placed at any convenient location, where such locations are known to those of skill in the art. In certain embodiments, a ground electrode or reference electrode is a scalp electrode. A scalp electrode may be placed on a subject's forehead or in any other convenient location.

Signal Processing

The signals received from the one or more electrodes are received and processed in real-time. Prior to the real-time processing, a signal is referred to herein as an "input signal," regardless of whether or not the signal itself is an output from any previous step. Input signals may originate from one or more electrodes. In certain embodiments, the electrodes are communicatively coupled to a processor apparatus that does the processing in real-time. The electrodes may also be in direct communication with a processor apparatus. In certain aspects, the electrodes may not be in direct physical communication with the processor, but may instead transmit the information by any convenient means. Of interest is wireless communication, a non-limiting example of which is described in US Patent Publication 2006/0129056; the disclosure of which is incorporated herein by reference.

Input signals may include a wide range of frequencies, which may depend upon factors including but not limited to the particular type of electrode employed, the type of subject, the position of the electrode, and other factors. In certain embodiments, an input signal may include frequencies of about 1 Hz to 500 Hz or more. In certain embodiments, an input signal may include frequencies from the range of about 1 to 10 Hz, about 10 to 20 Hz, about 20 to 30 Hz, about 30 to 40 Hz, about 40 to 50 Hz, about 50 to 60 Hz, about 60 to 70 Hz, about 70 to 80 Hz, about 80 to 90 Hz, about 90 to 100 Hz, about 100 to 125 Hz, about 125 Hz to 150 Hz, about 150 Hz to 175 Hz, about 175 Hz to 200 Hz, about 200 Hz to 225 Hz, about 225 Hz to 250 Hz, about 250 Hz to 275 Hz, about 275 Hz to 300 Hz, about 300 Hz to 325 Hz, about 325 Hz to 350 Hz, about 350 Hz to 375 Hz, about 375 Hz to 400 Hz, about 400 Hz to 425 Hz, about 425 Hz to 450 Hz, about 450 Hz to 475 Hz, or about 475 Hz to 500 Hz or more.

In some embodiments, input signals include delta, theta, alpha, mu, beta, gamma, or high gamma frequencies. Certain embodiments may include only one of delta, theta, alpha, mu, beta, gamma, and high gamma frequency bands. Other embodiments may include one or more of delta, theta, alpha, mu, beta, gamma, and high gamma frequency bands.

Figure 4:
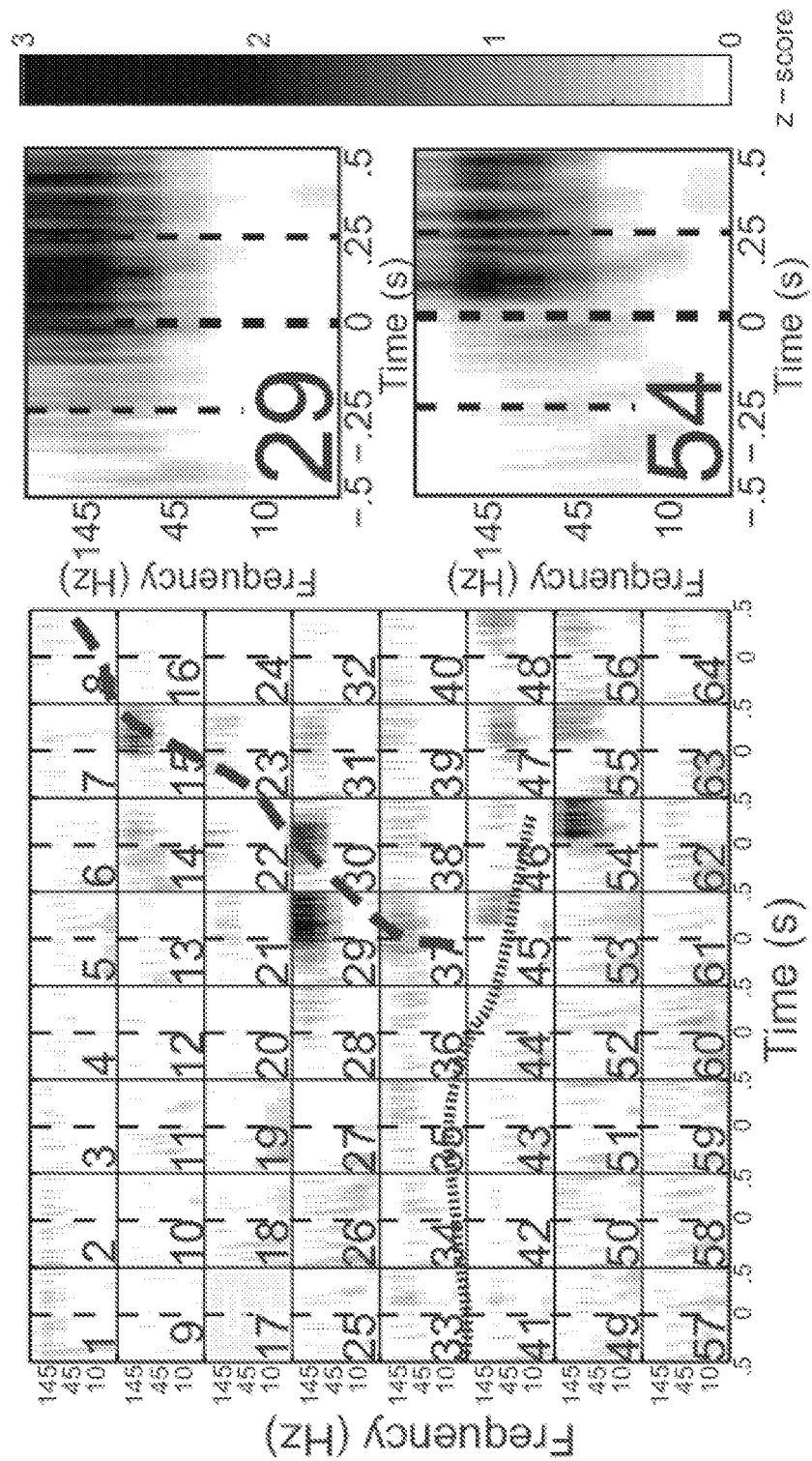
FIG. 4 depicts average event-related spectrograms for a subject. Each electrode is represented as a square on the 8×8 grid, and has its own separate time-frequency axes. The horizontal axis represents the progression of time, with the dotted line representing the onset of the event. Averaged data from half a second before the event, to half a second after the event is displayed. The 7 frequency bands are shown on the vertical axis (4-7, 8-12, 13-30, 31-59, 61-110, 111-179, 181-260 Hz). The average plot is shown for the evoked spectrograms when the subject repeated the syllable /la/ (Task 1) for approximately 1 minute. The central sulcus and Sylvian fissure are outlined with dashed and dotted lines, respectively. Spectrograms for specific channels are plotted on the right.

A feature of many embodiments is that the processing is in the absence of averaging based on time so as to provide separation of activation signals in sensory and motor cortices of the subject's brain. Averaging a signal across time discards temporal information that could be instrumental to understanding important dynamics, such as latency differences between activation in sensory and motor cortices. In contrast, many embodiments of the present disclosure do not incorporate such averaging of signal based on time. For example, FIG. 4 depicts a plot for when a subject was instructed to produce the syllable /la/. Electrodes 15, 29, and 30 in the ventral motor strip show strong activation that are clearly event-locked, and begins slightly before event onset (−118 ms), suggesting the motor planning for the articulation. It can be seen that electrode 54 in the posterior superior temporal gyms also reveals an increase in activity, however this only occurs after event onset (72 ms), and therefore is related to auditory sensory processing.

Such processing of an input signal may be performed by any convenient means, e.g. by analog, digital, or software means. In some embodiments, processing may be performed by a computer (e.g. laptop, desktop, server, cloud server, etc.) or neurophysiology workstation (e.g. a RZ2 Neurophysiology Workstation sold by Tucker Davis Technologies). Analog filtering may also be employed. In some instances, combination of processing means are employed, non-limiting examples of which may include, e.g., analog and digital filtering; digital and software filtering; and/or analog, digital, and software filtering.

In many embodiments, processing includes applying one filter or more to an input signal. A filter that is applied may be a notch filter. A notch filter may be applied any frequency for which signal subtraction is desired. In certain embodiments, a notch filter may be used that filters frequencies at about 60 Hz, at about 120 Hz, or about 180 Hz. A notch filter may be applied to remove electrical hum or other noise, such as that from an A/C current.

Processing may include applying a bandpass filter. A bandpass filter may be applied to an input signal prior to any other processing or filtering, or may be applied after other filtering or processing of an input signal has already taken place. A bandpass filter may separate a signal in about 2 to about 16 different frequency bands, or more. In certain embodiments, a bandpass filter may split a signal into about 2 frequency bands, about 4 frequency bands, about 6 frequency bands, about 8 frequency bands, about 10 frequency bands, about 12 frequency bands, about 14 frequency bands, about 16 frequency bands or more. In certain embodiments, a bandpass filter separates an input signal into about 7 different frequency bands. The 7 different frequency bands may include frequency ranges of about 4 to 7 Hz, about 8 to 12 Hz, about 13 to 30 Hz, about 31 to 59 Hz, about 61-110 Hz, about 111-179 Hz, and about 181 to 260 Hz. Specific frequency bands may be selected to divide a signal into physiologically important ranges. In some embodiments, a bandpass filter is employed to produce a signal including mu frequencies, beta frequencies, gamma frequencies, high gamma frequencies, or other ranges known to correspond to particular brain wave frequencies.

Processing may include applying a low-pass filter. A low-pass filter may be applied to an input signal prior to any other processing or filtering, or may be applied after other filtering or processing of an input signal has already taken place. In certain embodiments, a low-pass filter may be applied to the absolute value of a signal. The signal for which an absolute value is taken may have been filtered by a bandpass filter prior to the calculation of absolute value.

Processing may include approximating an envelope of a signal. Approximating an envelope may be applied to an input signal prior to any other processing or filtering, or may be applied after other filtering or processing of an input signal has already taken place. Approximating an envelope may be achieved by any convenient means, such as applying a Hilbert transform, a Fourier transform, or a low-pass filter to an absolute value of a signal. In many embodiments, approximating an envelope is in the absence of averaging based on time. In some aspects, processing may include adding baseline medians as constants to the incoming envelope amplitudes, taking the logarithm of the resulting sum to generate a symmetric Gaussian distribution of the log power, scaled by ½, and calculating the z-score of the Gaussian-distributed signal.

Processing may include calculating the phase of a signal. Calculating the phase of a signal may include any convenient means, such as a calculation using a Hilbert transform. Processing including calculating the phase of a signal may include, but is not limited to, methods described by Canolty, et al. (*Science,* 15 Sep. 2006: Vol. 313, pp. 1626-1628), the disclosure of which is incorporated herein by reference.

Processing may include calculating a power (e.g., log power, instantaneous power, etc.) of a signal. Calculating the power of a signal may include using a Fourier transform, and/or a wavelet transform.

Processing may be performed only one time, or may be performed more than one time on input signals. An input signal may be processed every 1 second or less. In certain embodiments, an input signal may be processed continuously, with such processing occurring for a particular duration of time, a particular number of iterations, or until the input signal is stopped.

Figure 3:
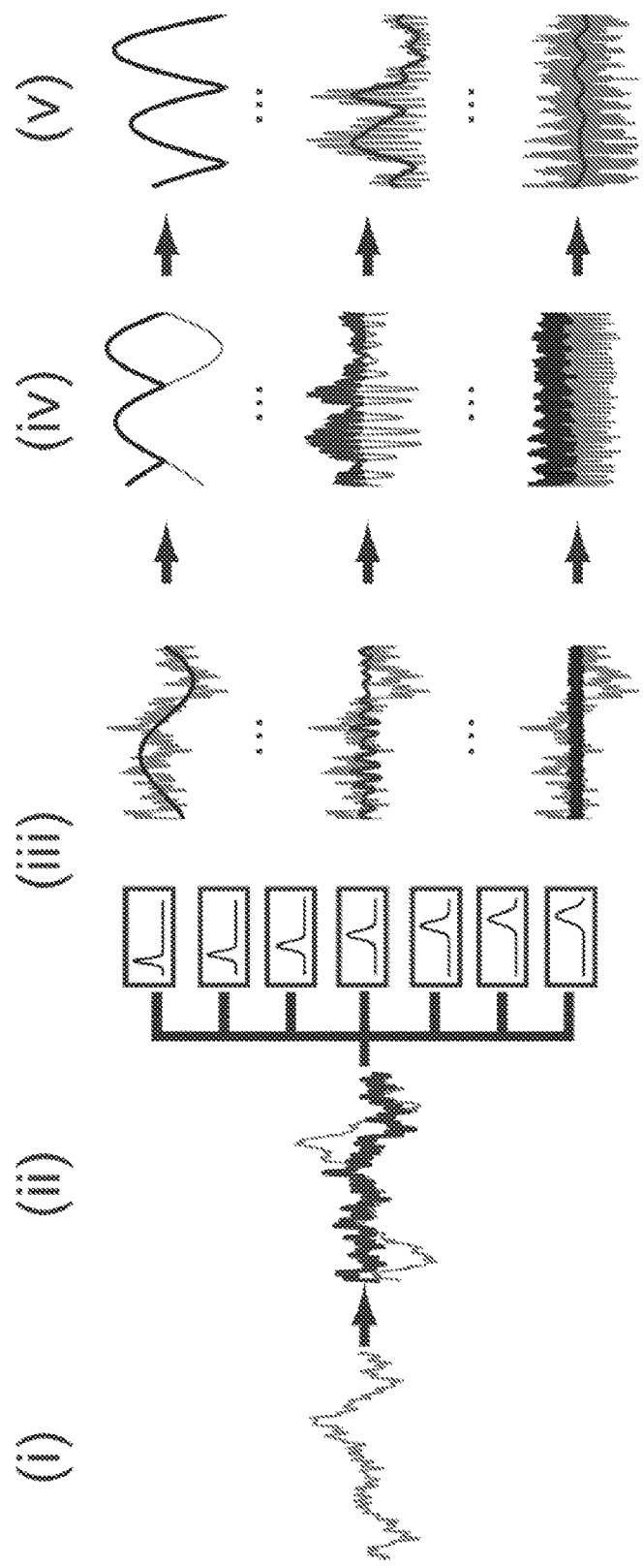
FIG. 3 depicts a non-limiting example of performing real-time processing of raw input ECoG signal. (i) An example of raw ECoG signal from a single channel is shown. (ii) Line noise is eliminated and the signal is re-referenced to the common average signal. (iii) The signal is separated by a filter bank (4-7 Hz, 8-12 Hz, 13-30 Hz, 31-59 Hz, 61-110 Hz, 111-179 Hz, and 181-260 Hz). (iv) The absolute value of the time series is taken. (v) The approximate amplitude envelope of the signal is extracted by low-pass filtering (cutoff frequencies: 5 Hz, 5 Hz, 20 Hz, 20 Hz, 40 Hz, 40 Hz, 40 Hz). The resulting signal after the stepwise process has been performed is shown in black. The preceding signal before the processing step is shown in grey.

Processing may include the steps illustrated in FIG. 3. In certain embodiments, raw data is obtained from each of a plurality of electrodes. Each channel, corresponding to data from an electrode, is notched and common average referenced. The data is then band pass filtered at 7 frequency bands. For each of the 7 frequency bands, the resulting signal (black) is absolute valued, and low pass filtered. Such processing may take place by analog, software, digital, or any other convenient means.

Output Device

Once an input signal is processed, it may be communicated to an output device. The phrase "output device" is intended to be used broadly and generically to refer to a device which may be used to display, processes, analyze, print, amplify, store, and/or utilize a processed signal. Illustrative but non-limiting examples of output devices may include a display monitor, a printer, a computer storage device (e.g. hard drive, tape drive, or other storage means), and other convenient output devices.

An output device may be configured to display a signal. In certain embodiments, displaying a signal may include processing the signal so that the output device displays the signal in a format convenient to the operator or surgeon.

In particular embodiments, signals may be visualized by adding baseline medians as constants to the incoming envelope amplitudes; taking the logarithm of the resulting sum to generate a symmetric Gaussian distribution of the log power, scaled by ½; calculating the z-score of the Gaussian-distributed signal; and displayed.

One illustrative example is that the signal may be displayed as an "average plot," which is used herein to describe a running average event-related spectrogram. It may calculated by summing all event-related spectrograms and dividing by the number of event trials. In other aspects, the average plot could also, or instead, be calculated using, e.g., median, mode, and the like. Since it is a running average, the spectrogram is recalculated and plotted with each event.

Figure 6:
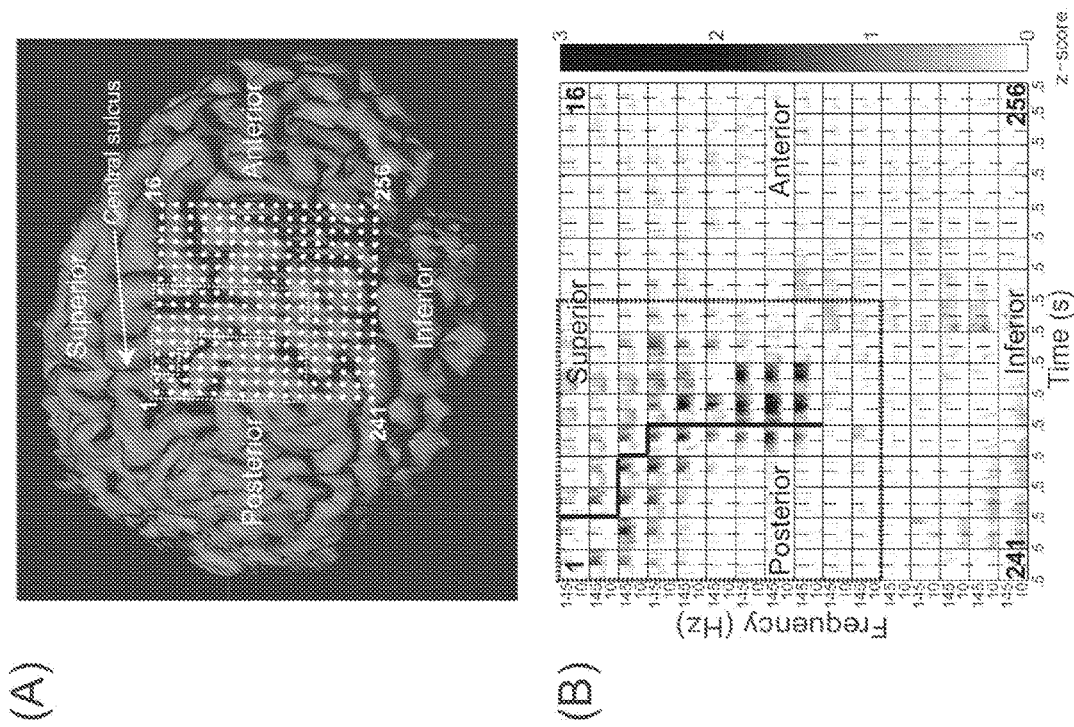
FIG. 6, Panels A-C depict ECoG grid superimposed on patient brain, average event-related spectrogram, and median nerve stimulation results. Panel A: A 256-channel subdural ECoG electrode array implanted over Subject E's right lateral hemisphere is shown. Electrodes are superimposed on the 3D MR surface reconstruction image. The boundary of the N20-P20 phase reversal is outlined. Panel B: Plots generated in real-time are shown depicting average event-related spectrograms during the button press task (Task 3). Each electrode is represented as a square on the 16×16 grid, and has its own separate time-frequency axes. The horizontal axis represents the progression of time, with the dotted line representing the onset of the event. Averaged data from half a second before the event, to half a second after the event is displayed. The 7 frequency bands are shown on the vertical axis (4-7, 8-12, 13-30, 31-59, 61-110, 111-179, 181-260 Hz). The boundary of the N20-P20 phase reversal is outlined. Panel C: Somatosensory evoked potentials gathered during median nerve stimulation are shown. Onset of stimulation is indicated with a dotted line at time 0 seconds. A phase reversal of the N20-P20 peak between a pair of electrodes indicates that the pair straddles the central sulcus. Dashed line potentials denote those that displayed a N20 peak during median nerve stimulation. Black potentials indicate a P20 peak was seen during stimulation. The boundary of the N20-P20 phase reversal is outlined.
Figure 6:
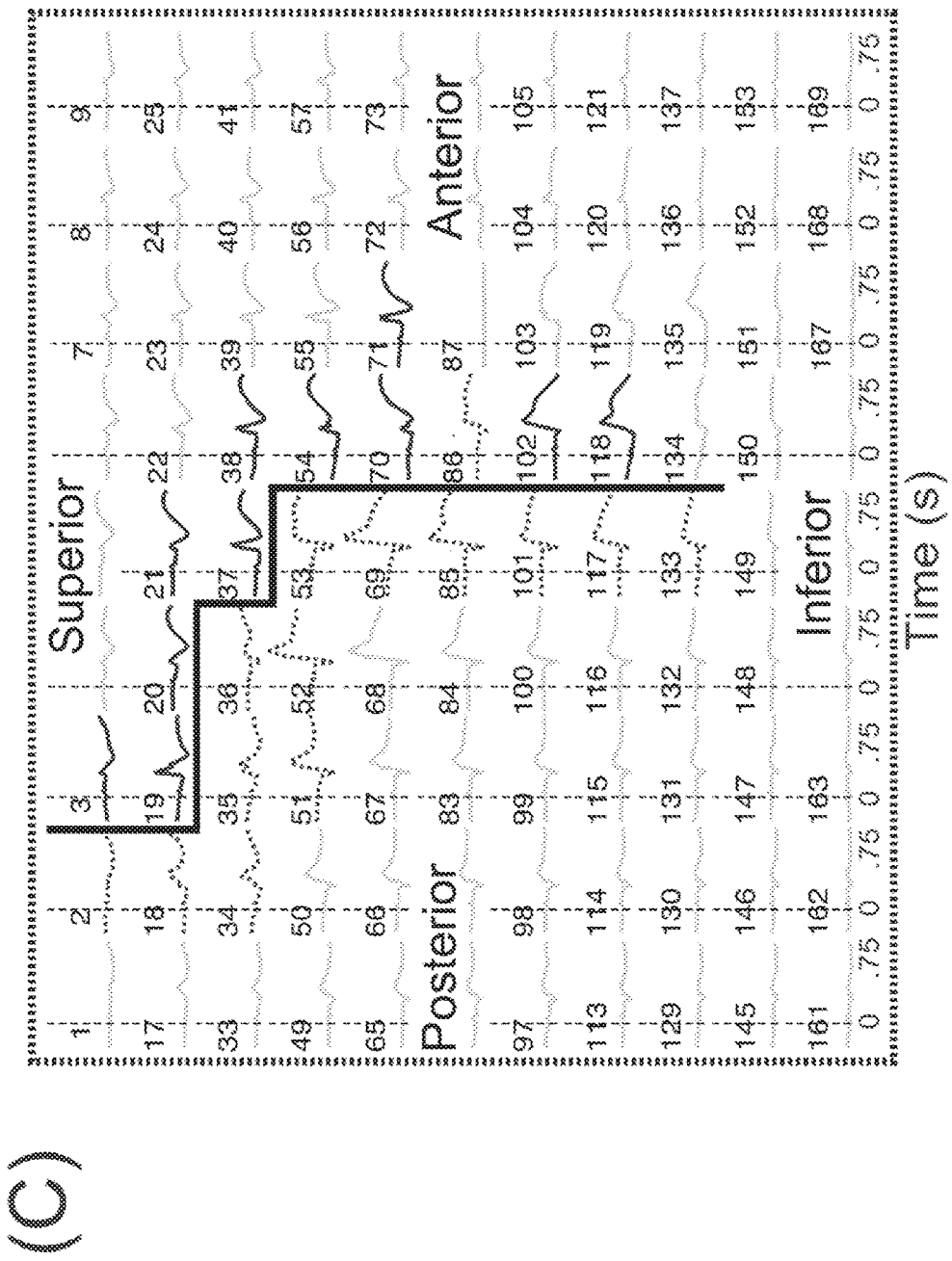

Two non-limiting examples of average plots are illustrated in FIGS. 4 and 6, Panel B. An average plot may include a plurality of boxes, with each box corresponding to data obtained from an electrode. In FIG. 4, for example, the upper left box corresponds to the electrode marked as 1 in FIG. 2. Data presented in this box shows the frequency (y-axis) plotted along with time (x-axis). The x-axis time scale starts at a period before an event, which is delineated at time=0, and continues until after the event. Higher z-scores within a certain box can be used to indicate that a particular channel had increased activity at a particular time. Conversely, lower z-scores within a particular box can be used to indicate that a particular channel had decreased activity at a particular time.

Turning to more specific examples, in FIG. 4 the average plot is shown for when the subject was instructed to produce the syllable /la/. Electrodes 15, 29, and 30 in the ventral motor strip show strong activation that are clearly event-locked, and begins slightly before event onset (−118 ms), suggesting the motor planning for the articulation. It can be seen that electrode 54 in the posterior superior temporal gyms also reveals an increase in activity, however this only occurs after event onset (72 ms), and therefore is related to auditory sensory processing.

In FIG. 6, Panels A-C, the utility of real-time spectral mapping of sensory and motor organization for the hand is shown. Subject E was implanted with a 256 channel array over the right peri-Rolandic cortex (FIG. 6, Panel A). The average plot was generated in real-time while subject E was pressing a button with his left thumb (FIG. 6, Panel B). Electrodes along the central sulcus can be rapidly visually identified to have an event-related increase in the high gamma power (61-260 Hz), and an event-related decrease in alpha power (4-12 Hz). The anterior ventral-most electrodes showed high gamma activation onset nearly 200 milliseconds prior to the button press, consistent with the precentral gyms cortical motor processing specifically for the thumb which is the most ventral representation in the homunculus. In contrast, the posterior electrodes showed somatosensory activation after the button press. Using median nerve stimulation, the typical N20-P20 phase reversal in the averaged evoked potentials is observed along the central sulcus (FIG. 6, Panel C), and confirmed the localization mapping from real time spectral mapping. Note that median nerve stimulation is not exactly identical to thumb movement alone in the button press, which may explain some of the minor differences in localization between the plots.

Figure 7:
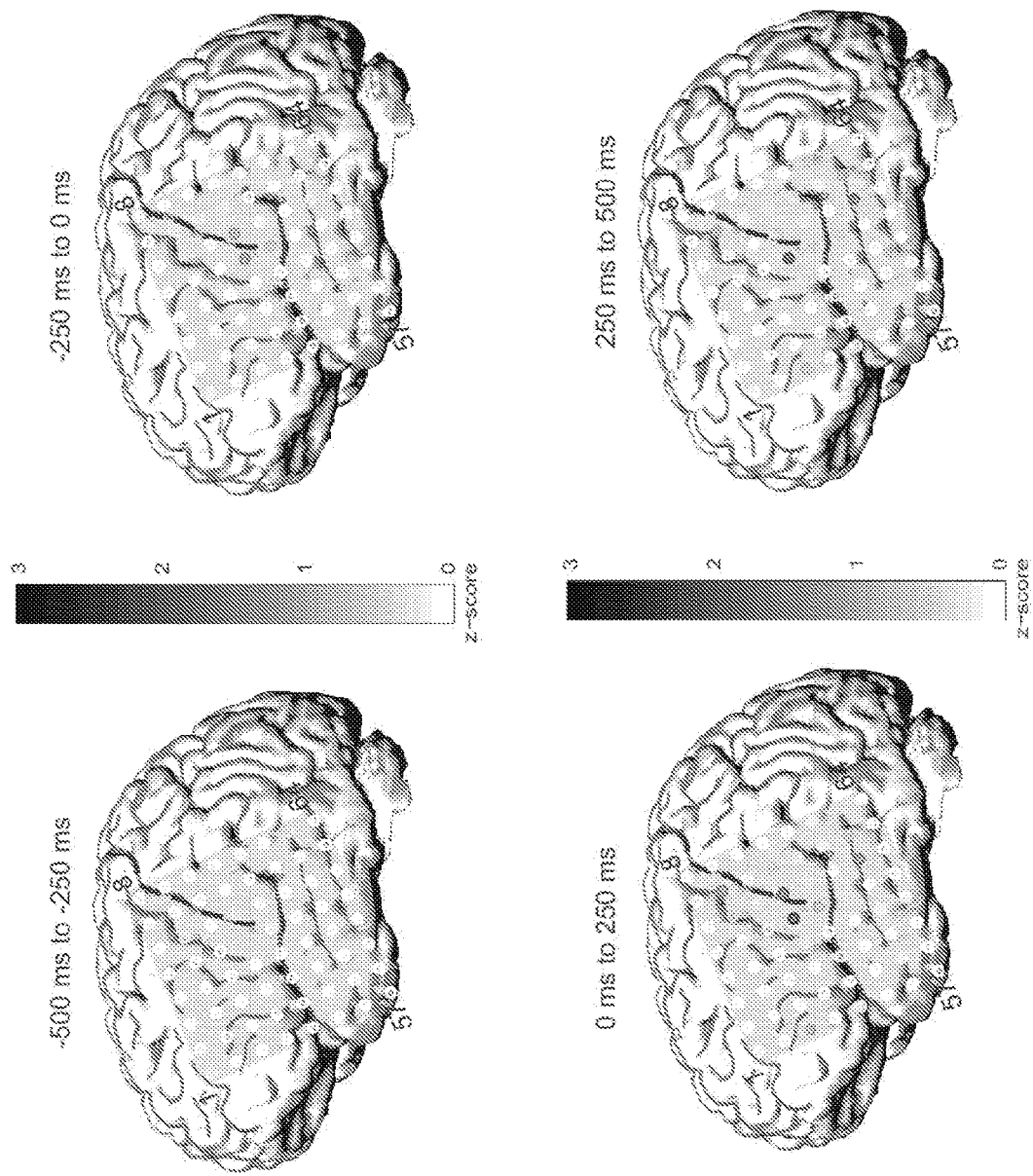
FIG. 7 shows average activity at different time epochs on MRI surface reconstruction. Plots generated in real-time depict average event-related high gamma (61-260 Hz) activations on subject A's 3D MRI surface reconstruction image at four different time intervals (−500 to −250 ms, −250 to 0 ms, 0 to 250 ms, 250 to 500 ms) during production of the syllable /la/. The central sulcus and Sylvian fissure are outlined with dashed and dotted lines, respectively.

In order to provide an intuitive visualization which readily relates activity to anatomical regions, the magnitude of the running average event-related high gamma (61-260 Hz) activations at four different time intervals (−500 to −250 ms, −250 to 0 ms, 0 to 250 ms, 250 to 500 ms) was projected on to the subject's 3D MRI surface reconstruction image, and updated after every trial. Plots from the same speech production task (/la/) are shown in FIG. 7. It can be easily seen which electrodes are active immediately before and after the event onset, and where they are located on the subject's individual brain. The four separate time epochs allow one to distinguish the pre-event motor from post-event sensory cortical activations.

Figure 5:
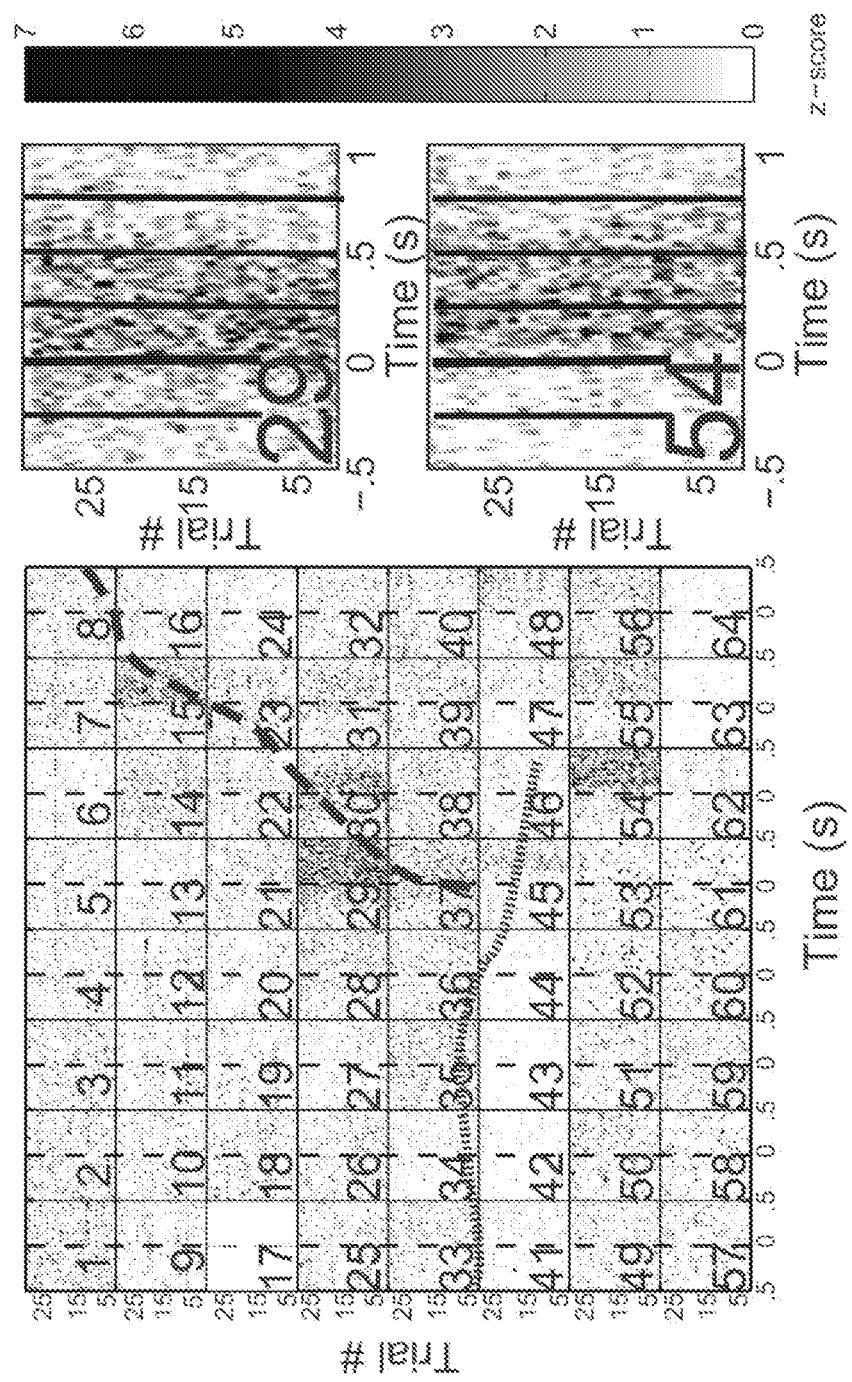
FIG. 5 depicts single-trial raster plots for Subject A's 8×8 electrode grid (i.e., the grid shown in FIG. 2). Each electrode has its own separate time axes. The horizontal axis represents the progression of time, with the dotted line representing the onset of the event. Data from half a second before the event, to half a second after the event are displayed. On the vertical axis are each event's activations in one frequency band (111-179 Hz). Z-score deviations from baseline are in grayscale. This raster plot was generated after the subject produced the syllable /la/ for approximately 1 minute. The central sulcus and Sylvian fissure are outlined with dashed and dotted lines, respectively. Rasters for specific channels are plotted on the right. The time axis has been extended to show a full second after the event.

Another illustrative example is a "single-trial raster plot," which is used herein to describe single trial activations in a stacked raster plot. A single-trial raster plot may display cumulative single trials spectral changes for a given frequency range measured in z-score deviations from the baseline. FIG. 5 presents a non-limiting example of a single trial raster plot. On the y-axis is plotted a trial number, while the x-axis is time. As with the average plot, the x-axis scale may start at a period before an event, which is delineated at time=0, and may continue until after the event. In FIG. 5, the stacked single trial plot was generated simultaneously with the same speech production task (/la/) displayed in FIG. 4. For each new event the plot is updated with the single event trial added as a horizontal row; FIG. 5 shows data for the range 111-179 Hz. The patterns observed across events demonstrate the robustness of the physiologic approach in single trials, and adds another visualization that does not require averaging which can be susceptible to outlier values. Key channels from the stacked plot can be more carefully examined on the right. Note the time axis has been extended to show a full second after the event. Again, these plots demonstrate that activity occurs earlier in the motor electrodes compared to the sensory auditory channels.

Figure 10:
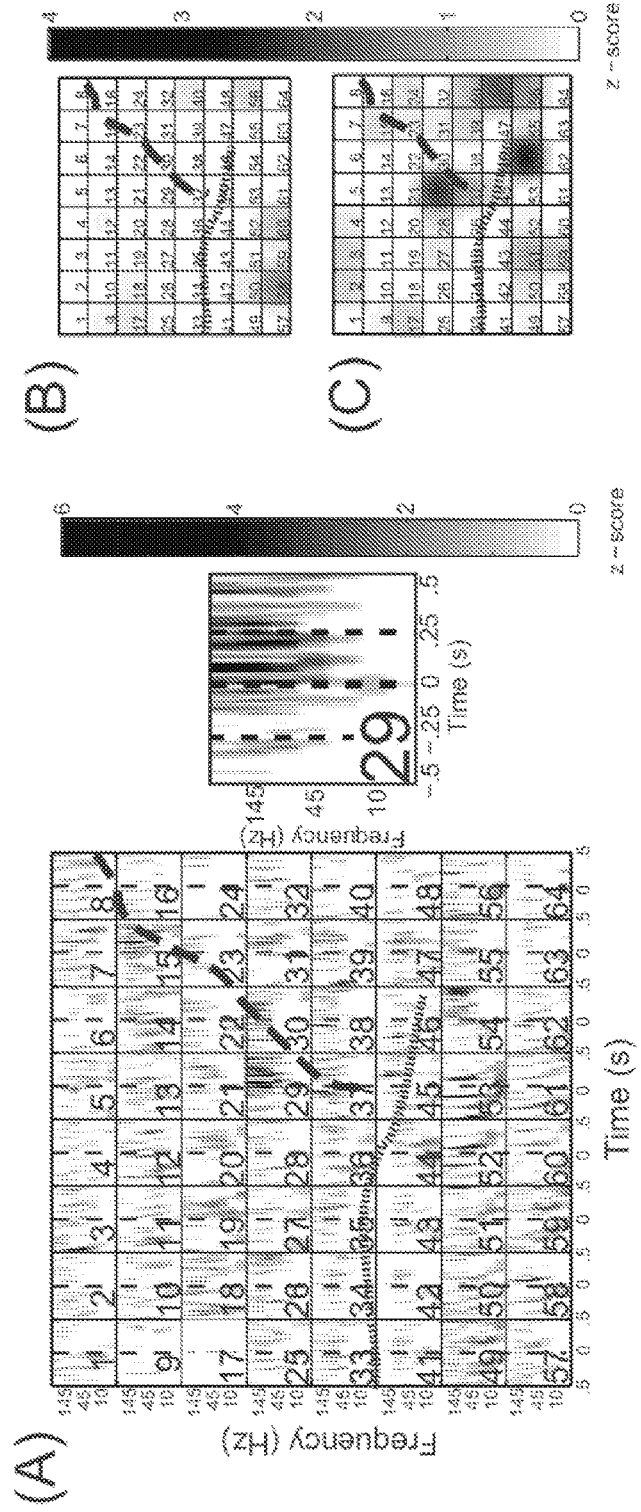
FIG. 10, Panels A-C show single-trial event-related spectrograms and continual plots. Panel A: Plots are shown depicting event-related spectrograms for one event during Subject A's /la/ task. On the left, each electrode is represented as a square on the 8×8 grid with the same time-frequency axis used in the average plot (FIG. 4). On the right is a spectrogram for channel 29. High event-locked z-scores can be seen, especially in channel 29. In offline analyses the maximum z-score in channel 29's single-event spectrogram was found to be significant using a Bonferroni-corrected alpha level of 0.05 ($p<1.9\times10^{-4}$, 181-260 Hz, t=44 ms). While this significant activation in channel 29 corresponds well with observations made with the average and single-trial raster plots, a broad range of activations throughout the grid (dark gray coloring) makes it difficult to visually identify other crucial channels with the single-event spectrograms. Panels B, C: Plots are shown depicting average z-scores of 20 ms of data during Subject A's /la/ task in the 111-179 Hz spectral range. Each electrode is represented as a square on the 8×8 grid. Shown are average z-scores captured during a period of rest (Panel B) and during the production of syllable /la/ (Panel C). During rest nearly all electrodes to have insignificant p-values ($p>0.87$, Bonferroni-corrected). During speech production, channels 29 and 54 show a high change from baseline. These channels correspond to those identified in the average plots (FIG. 4). However, channels 15 and 30, seen activated in the average plot, do not show similar changes. The central sulcus and Sylvian fissure are outlined with dashed and dotted lines, respectively.

Yet another illustrative example is a "single plot," which is used herein to refer to an event-related spectrogram of the most recent single event trial. In the single plot, the most recent event spectrogram is shown. FIG. 10, Panel A shows one such plot from a subject's /la/ task. High event-locked z-scores can be seen, especially in channel 29. In offline analyses the maximum z-score in channel 29's single-event spectrogram was found to be significant (z-score=5.44, p-value<$2.6 \times 10^{-8}$, alpha-level<0.0001, 181-260 Hz, t=44 ms). While this significant activation in channel 29 corresponds well with observations made with the average and single-trial raster plots, a broad range of activations throughout the grid (black-dark gray coloring) makes it difficult to visually identify other crucial channels with the single-event spectrograms.

Another illustrative example is a "continual plot," used herein to describe a plot of mean z-score of the last desired period of time of data from a specified frequency. Average z-scores of the most recent 20 ms from the grid in the 111-179 Hz band are displayed and refreshed with every iteration in the continual plot. Two such plots from the subject's production of /la/ task are shown below. In FIG. 10, Panel B was captured during a period of rest and shows nearly all electrodes to have insignificant z-scores (range: $|z|<1.5$, p-value=0.87, alpha-level<0.05). FIG. 10, Panel C was produced during an event and shows a high change from baseline in channels 29 and 54. These channels correspond to those identified in the average plots (FIG. 2). However, channels 15 and 30, seen activated in the average plot, do not show similar changes.

Accordingly, an output device may include or display one or more of the plots described above.

Repetition/Iteration

As illustrated in FIG. 1, the steps of receiving signals from electrodes 104, processing signals in real time 106, and communicating processed signal to an output device 108 may be repeated or iterated 110. The particular number of iterations may be determined by, for example, a particular duration of time, particular number of iterations, or until the input signal is stopped.

In many embodiments, a subject performs a task while such iterations take place. The subject may be asked or directed to perform the task, while in some embodiments the subject performs a task without direction. Example tasks may include motor, sensory, or other tasks. For example, a task may be, but not be limited to, a speaking task, a listening task, a hand button press, or tactile somatosensation.

A speaking task may involve production of a particular syllable, such as /ba/ or /la/. In certain instances, a speaking task may involve production of more than one syllable, such as words, phrases, sentences, paragraphs, or more. An element of speaking tasks is that the subject be the one to produce a sound.

A listening task may involve simple passive listening to a particular sound. In some embodiments, an experimenter produces the sound, and may produce a simple sound such as /ba/ or /la/ syllables. In other instances, a listening task may involve one or more speakers producing more than one syllable, such as words, phrases, sentences, paragraphs, or more. In other instances, a listening task may involve a subject listening to material produced from or amplified by any convenient electronic means, such as a radio, television, computer, phonograph, etc.

A hand button press task may involve the subject pressing a button with his or her hand. The phrase "hand button press task" is meant herein broadly and generically to refer to any task wherein a subject triggers a response through a physical contact with a trigger, through any part of his or her body. For example, a non-limiting example of a hand button press task may involve a rodent pressing a lever with a paw. Another example may be a human pressing a button with her hand.

Yet another type of task may be a tactile somatosensation task. In such a task, a subject may respond to a tactile somatosensation. Such somatosensation may be provided by any convenient means.

It is often desirable that one task may be performed more than one time. In such cases, iterations may continue while a subject performs a task more than one time. The tasks may be performed substantially continuously, or there may be an interval between the tasks being performed. In many embodiments, there is about 1 s to 5 m between tasks.

A subject may perform more than one type of task while iterations continue. In such cases, any number and composition of tasks may be possible. The tasks may be performed substantially continuously, or there may be an interval between the tasks being performed. In many embodiments, there is about 1 s to 5 m between tasks.

Iterations may commence prior to a subject performing a task, after a subject performs a task, or coincident with a subject performing a task. In certain aspects, baseline information may be gathered prior to a subject performing the task. Baseline information may be gathered in any convenient means. For example, baseline information may be gathered as described by Chang, et al. (Cortical Spatiotemporal Dynamics Underlying Phonological Target Detection in Humans, *Journal of Cognitive Neuroscience*, 2011), the disclosure of which is incorporated herein by reference. In other aspects, when iterations commence prior to a subject performing a task, the iterations may commence for a short period beforehand so as to establish a baseline measurement prior to the task. The duration of time prior to the task may be any practicable time, such as about 1 ms or more, about 10 ms or more, about 50 ms or more, about 100 ms or more, about 250 ms or more, about 500 ms or more, about 750 ms or more, about 1 s or more, about 5 s or more, about 10 s or more, about 30 s or more, about 1 m or more, about 2 m or more, about 5 m or more, or about 10 m or more.

Iterations may continue for a period after a subject performs a task. Again, the duration of time may be any practicable time, such as about 1 ms or more, about 10 ms or more, about 50 ms or more, about 100 ms or more, about 250 ms or more, about 500 ms or more, about 750 ms or more, about 1 s or more, about 5 s or more, about 10 s or more, about 30 s or more, about 1 m or more, about 2 m or more, or about 5 m or more.

When iterations are calculated, an output device may display prior results, the current results, an average of current results and prior results, or any other convenient combination.

In certain instances, a subject may perform or be directed to perform more than one task concurrently. For example, a subject may perform a speaking task while also performing a hand button press task; a subject may perform a hand button press task while performing a listening task; a subject may perform a listening task while performing a tactile somatosensation task, etc. Any possible permutation of the above-mentioned tasks may be possible. In certain instances, a subject may perform one or more tasks individually. A subject may perform the one or more tasks roughly concurrently. Differences between the output from when the subject performed a task individually may be compared or otherwise analyzed to when a subject performed tasks concurrently. In certain instances, such information may be used to analyze higher-order cortical mapping patterns than would be accessible or practicable from individual tasks.

Indicating a Subject's Response to an Agent

In particular embodiments, the methods of the present disclosure are utilized to indicate a subject's reaction to an agent. Such embodiments may include positioning a plurality of electrodes to detect a subject's brain activity; receiving a first plurality of input signals indicative of a subject's brain activity; performing real-time processing of the first plurality of input signals by applying a filter to the plurality of input signals, wherein the processing is in the absence of averaging based on time so as to provide separation of activation signals in sensory and motor cortices of the subject's brain; administering an agent to the subject; receiving a second plurality of input signals indicative of the subject's brain activity; performing real-time processing of the second plurality of input signals by applying a filter to the second plurality of input signals, wherein the processing is in the absence of averaging based on time so as to provide separation of activation signals in sensory and motor cortices of the subject's brain; and identifying physiological information concerning the subject based upon differences between the first plurality of signals and the second plurality of signals.

In other embodiments, such methods include positioning a plurality of electrodes to detect a subject's brain activity; receiving a first plurality of input signals indicative of a subject's brain activity; performing real-time processing of the first plurality of input signals by applying a filter to the plurality of input signals; administering an agent to the subject; receiving a second plurality of input signals indicative of the subject's brain activity; performing real-time processing of the second plurality of input signals by applying a filter to the second plurality of input signals; and identifying physiological information concerning the subject based upon differences between the first plurality of signals and the second plurality of signals.

As used herein, "agent" or "drug" or any similar term is used broadly and generically herein to refer to any stimulation (e.g. electrical stimulation), drug or any chemical or biological material or compound suitable or other beneficial agent which it is desired to deliver to a subject, and the present invention is not limited to any particular agents. For illustrative purposes only, this includes but is not limited to anaesthetics; analgesics; cell transport/mobility impending agents such as colchicines, vincristine, cytochalasin B and related compounds; carbonic anhydrase inhibitors such as acetazolamide, methazolamide, dichlorphenamide, diamox and neuroprotectants such as nimodipine and related compounds; antibiotics such as tetracycline, chlortetracycline, bacitracin, neomycin, polymyxin, gramicidin, cephalexin, oxytetracycline, chloramphenicol, rifampicin, ciprofloxacin, aminosides, gentamycin, erythromycin and penicillin; quinolone; ceftazidime; vancomycine imipeneme; antifungals such as amphotericin B, fluconazole, ketoconazole and miconazole; antibacterials such as sulfonamides, sulfadiazine, sulfacetamide, sulfamethizole and sulfisoxazole; nitrofurazone and sodium propionate; antivirals, such as idoxuridine, trifluorothymidine, trifluorouridine, acyclovir, ganciclovir, cidofovir, interferon, DDI, AZT, foscamet, vidarabine, irbavirin, protease inhibitors and anti-cytomegalovirus agents; antiallergenics such as sodium cromoglycate, antazoline, methapyriline, chlorpheniramine, cetirizine, pyrilamine and prophenpyridamine; synthetic gluocorticoids and mineralocorticoids and more generally hormones forms derivating from the cholesterol metabolism (DHEA, progesterone, estrogens); non-steroidal antiinflammatories such as salicylate, indomethacin, ibuprofen, diclofenac, flurbiprofen, piroxicam and COX2 inhibitors; antineoplastics such as carmustine, cisplatin, fluorouracil; adriamycin, asparaginase, azacitidine, azathioprine, bleomycin, busulfan, carboplatin, carmustine, chlorambucil, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, florxymesterone, flutamide, goserelin, hydroxyurea, ifosfamide, leuprolide, levamisole, limustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine; immunological drugs such as vaccines and immune stimulants; insulin, calcitonin, parathyroid hormone and peptide and vasopressin hypothalamus releasing factor; beta adrenergic blockers such as timolol, levobunolol and betaxolol; cytokines, interleukines and growth factors epidermal growth factor, fibroblast growth factor, platelet derived growth factor, transforming growth factor beta, ciliary neurotrophic growth factor, glial derived neurotrophic factor, NGF, EPO, PLGF, brain nerve growth factor (BNGF), vascular endothelial growth factor (VEGF) and monoclonal antibodies or fragments thereof directed against such growth factors; antiinflammatories such as hydrocortisone, dexamethasone, fluocinolone, prednisone, prednisolone, methylprednisolone, fluorometholone, betamethasone and triamcinolone; decongestants such as phenylephrine, naphazoline and tetrahydrazoline; miotics and anti-cholinesterases such as pilocarpine, carbachol, di-isopropyl fluorophosphate, pholine iodine and demecarium bromide; mydriatics such as atropine sulphate, cyclopentolate, homatropine, scopolamine, tropicamide, eucatropine; sympathomimetics such as epinephrine and vasoconstrictors and vasodilators, anticlotting agents such as heparin, antifibrinogen, fibrinolysin, anticlotting activase, antidiabetic agents include acetohexamide, chlorpropamide, glipizide, glyburide, tolazamide, tolbutamide, insulin and aldose reductase inhibitors, hormones, peptides, nucleic acids, saccharides, lipids, glycolipids, glycoproteins and other macromolecules include endocrine hormones such as pituitary, insulin, insulin-related growth factor, thyroid, growth hormones; heat shock proteins; immunological response modifiers such as muramyl dipeptide, cyclosporins, interferons (including alpha-, beta-and gamma-interferons), interleukin-2, cytokines, tumor necrosis factor, pentostatin, thymopentin, transforming factor beta2, erythropoetin; anti-angeogenesis proteins (e.g. anti VEGF, interferons), antibodies (monoclonal, polyclonal, humanized, etc.) or antibodies fragments, oligoaptamers, aptamers and gene fragments (oligonucleotides, plasmids, ribozymes, small interference RNA (siRNA), nucleic acid fragments, peptides), immunomodulators such as endoxan, thalidomide, tamoxifene; antithrombolytic and vasodilator agents such as rtPA, urokinase, plasmin; nitric oxide donors, nucleic acids, dexamethasone, cyclosporin A, azathioprine, brequinar, gusperimus, 6-mercaptopurine, mizoribine, folic acid analogs (e.g., denopterin, edatrexate, methotrexate, piritrexim, pteropterin, Tomudex(R), trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, and prednislone; anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; tranquilizers; and nicotine and acid addition salts thereof.

Systems

Also provided are systems for cortical mapping in real-time. In certain embodiments, a cortical mapping system includes a plurality of electrodes; a processor; and a machine-readable medium encoding instructions operable to cause the processor to perform real-time operations including: obtaining, from the plurality of electrodes, a plurality of brain signals of a subject; processing each sensed brain signal by applying a filter to the brain signal, wherein the processing is in the absence of averaging based on time so as to provide separation of activation signals in sensory and motor cortices of the subject's brain; and identifying physiological information concerning the subject based on the plurality of processed sensed brain signals.

A number of other components may also be included in systems of the present disclosure. For example, systems may include a processing system, which generally comprises at least one processor or processing unit or plurality of processors, memory, and at least one output device, coupled together via a bus or group of buses. The memory can be any form of memory device, for example, volatile or non-volatile memory, solid state storage devices, magnetic devices, etc. The processor can comprise more than one distinct processing device, for example to handle different functions within the processing system.

In use, the processing system may be adapted to allow data or information to be stored in and/or retrieved from, via wired or wireless communication means, at least one database. The interface may allow wired and/or wireless communication between the processing unit and peripheral components that may serve a specialized purpose. In general, the processor can receive instructions as input data via input device and can display processed results or other output to a user by utilizing output device. More than one input device and/or output device can be provided. A processing system may be any suitable form of terminal, server, specialized hardware, or the like.

A processing system may be a part of a networked communications system. A processing system can connect to a network, for example the Internet or a WAN. Input data and output data can be communicated to other devices via the network. The transfer of information and/or data over the network can be achieved using wired communications means or wireless communications means. A server can facilitate the transfer of data between the network and one or more databases. A server and one or more databases provide an example of an information source. Thus, a processing computing system environment may operate in a networked environment using logical connections to one or more remote computers. The remote computer may be a personal computer, a server, a router, a network PC, a peer device, or other common network node, and typically includes many or all of the elements described above.

Certain embodiments may be described with reference to acts and symbolic representations of operations that are performed by one or more computing devices. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting, as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, programmable consumer electronics, network, minicomputers, server computers, web server computers, mainframe computers, and distributed computing environments that include any of the above systems or devices.

The present disclosure also provides computer program products that, when executed on a programmable computer such as that described above, can carry out the methods of the present disclosure. As discussed above, the subject matter described herein may be embodied in systems, apparatus, methods, and/or articles depending on the desired configuration. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. electrode(s), video camera, microphone, joystick, keyboard, and/or mouse), and at least one output device (e.g. display monitor, printer, etc.).

Computer programs (also known as programs, software, software applications, applications, components, or code) include instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, etc.) used to provide machine instructions and/or data to a programmable processor, including a machine-readable medium that receives machine instructions as a machine-readable signal.

It will be apparent from this description that aspects of the present invention may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium including any type of ROM, RAM, cache memory, network memory, floppy disks, hard drive disk (HDD), solid-state devices (SSD), optical disk, CD-ROM, and magnetic-optical disk, EPROMs, EEPROMs, flash memory, or any other type of media suitable for storing instructions in electronic format.

In addition, the processor(s) may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices. In alternative embodiments, special-purpose hardware such as logic circuits or other hardwired circuitry may be used in combination with software instructions to implement the techniques described herein.

Utility

The methods and systems of the present disclosure find use in a variety of different applications where it is desirable to perform cortical mapping. For example, the methods and systems can be used to analyze epileptic foci and to classify functional brain areas, such as language centers. The subject systems and methods may be used to guide surgical procedures. Additionally, the methods and systems of the present disclosure find use in applications where it is desirable to indicate a subject's response to administration of an agent.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Methods and Materials

The following are general materials and protocols used in the Examples below.

Subjects

ECoG was recorded in 5 refractory epilepsy patients (see Table 1) undergoing intracranial monitoring for the localization of an epileptogenic focus. All subjects underwent a craniotomy for chronic (1-2 weeks) implantation of a subdural platinum-iridium electrode array over the left hemisphere. The study protocol, approved by the UC San Francisco Committee on Human Research, presented minimal risk to participating subjects and did not interfere with the clinical ECoG recordings. Placement of the array was determined entirely by clinical needs and varied between subjects. All participants provided informed consent.

Where required, subject-specific figures were generated from Subject A. Using anatomic image fusion software from BrainLab (Munich, Germany), electrode positions were extracted by computed tomography (CT) scan, co-registered with the patient's MRI, and then superimposed on the subject's 3D MRI surface reconstruction image (FIG. 2). Registrations were verified with intraoperative photographs, and by another third-party open-source imaging software, Osirix.

Example 1: Real-Time Cortical Mapping

Materials and Methods:
Signal Acquisition
ECoG recording was carried out using a portable customized multichannel neurophysiology workstation (Tucker-

TABLE 1

Patient Characteristics

| Subject | Age | Gender | Hemispheric coverage | Epilepsy Type | Age of Seizure Onset | Resection Location | Engel Seizure Outcome Classification | Hemispheric Dominance for Language (Wada) | Major cognitive deficits |
|---|---|---|---|---|---|---|---|---|---|
| A | 23 | M | Left | Focal | 3 | Temporal lobe | I | Left | No |
| B | 36 | F | Left | Focal | 18 | Inferior parietal lobe | II | Left | No |
| C | 48 | M | Left | Focal | 2 | Anterior temporal lobe | I | Left | No |
| D | 45 | M | Left | Focal | 24 | Posterior temporal cortex | I | Left | No |
| E | 30 | M | Right | Focal | 7 | Inferior parietal cortex | III | Left | No |

Experimental Setup

Subdural ECoG grids were standard 64-channel platinum-iridium electrodes with 10 mm center-to-center spacing arranged in an 8×8 configuration (Ad-Tech, Racine, Wis., USA). Each electrode had an exposed diameter of 2 mm Subject E received a high-density 256-channel grid with 4 mm center-to-center spacing over the right hemisphere. Each electrode had exposed diameter of 1.25 mm.

ECoG signals were split between the clinical monitoring system and a customized research data acquisition and processing system. The ground and reference were a scalp electrode, usually on the patient's forehead. A 30 second baseline period dataset was collected. During this baseline period, the room was quieted and subjects were instructed to simply rest with eyes open and without moving. Generally, only one baseline collection was needed per day of experimentation; however, multiple were often collected for post-hoc comparisons, or if there was a long interval between data collection periods.

Experimental sessions were divided into blocks, each lasting 1-2 min. There were four simple tasks designed to illustrate the algorithm: 1) Speaking, 2) Listening, 3) Hand button press, 4) Tactile somatosensation. The speaking task involved self-paced production of /ba/ and /la/ syllables. A listening task involved simple passive listening to the experimenter's repeated production of /ba/ or /la/ syllables.

The third task required the subject to press a handheld button press device with the thumb of the contralateral hand. Subjects were instructed to press the button when a cue was presented. The cue in this particular paradigm was whenever the experimenter raised his right hand, as opposed to the left hand. The experimenter randomly raised either left or right hand throughout this trial. In the fourth task, to isolate the somatosensory response, the experimenter briefly applied the same button press device against the subject's finger while the subject was resting. These blocks consisted of 15-40 events.

Davis Technologies, TDT, Alachua, Fla., USA). All channel signals were amplified independently. The data was sampled at 500 Hz and recorded in a circular buffer for real-time analysis.

Real-time Signal Processing

Real-time signal processing was carried out on the portable workstation. To ensure that signals analyzed contained no ambient electrical line noise, 60 Hz and its harmonics were removed using a second-order Butterworth notch filter with a 5 Hz stopband. The common average reference was removed from each channel by subtracting the average of the raw signal across all electrodes. Electrode channels were omitted if they, upon visual inspection, had poor signal quality due to electrode drift, poor electrode contact, or excessive high frequency noise. Following the re-referencing, the signal was band pass filtered at seven different frequency bands (4-7 Hz, 8-12 Hz, 13-30 Hz, 31-59 Hz, 61-110 Hz, 111-179 Hz, and 181-260 Hz) using a second-order Butterworth filter. The resulting bandpass signals can be viewed as carrier signals whose amplitudes are modulated by slower periodic signals.

The slower periodic signal can be extracted by approximating the envelope of the bandpass signal. This was done by low-pass filtering the absolute value of the resulting signal. Since the cutoff frequency of a modulating signal is always at most half the bandwidth of the bandpass signal, frequency cutoffs were set at 5, 20 and 40 Hz for signals band passed filtered between 4-12, 13-59 and 61-260 Hz, respectively. A diagram of the preprocessing stream can be seen in FIG. 3.

Event Detection

A basic event detection method was implemented in order to determine the timing of cortical events related to the execution of a particular task. Both speaking and listening events were recorded using a microphone. For the hand movement and somatosensory tasks, a simple button press device was used. Both analog signals were recorded simultaneously and synchronously with the multichannel ECoG data. The signal was converted to a digital signal and downsampled to 500 Hz and smoothed using an exponential smoothing average with a factor of 0.005. Threshold voltages were predetermined for the outputs of the microphone at 80 dB sound pressure level (SPL) and the button press device. Event onset was defined to be the time when analog voltages exceeded a pre-defined threshold voltage. To ensure that inaccuracy in event detection did not skew any results, any experimental session was discarded where false events (e.g. coughing) were registered.

Visualization

Matlab (Mathworks, Natick, Mass., USA) was used for visualization and to create a user interface. The envelope of the ECoG signal and event signal were used as inputs.

To examine the event-related change in ECoG activity, the neural signal was normalized with respect to the baseline rest signal. The log power of the signal was first calculated by taking the logarithm of the incoming envelope signal. To avoid taking the logarithm of 0, which is undefined, the median envelope signals during the baseline period were added as constants prior to taking the logarithm. The log power was then z-score normalized using the mean and standard deviation of the baseline log power signal.

During the task, five plots of the entire electrode grid were continuously refreshed. This means the software was set to read and analyze newly acquired data immediately after the previous cycle was completed. Each cycle took on average 0.7 seconds to complete. Listed below are names and descriptions of the plots. Each plot takes approximately 0.15 seconds to calculate and display.

1) Average plot: Displays the running average event-related spectrogram. It is calculated by summing all event-related spectrograms and dividing by the number of event trials. Since it is a running average, the spectrogram is recalculated and plotted with each event.
2) Average plot on MR: Displays running average event-related activations on the subject's 3D MRI surface reconstruction image.
3) Single-trial raster plot: Displays single trial activations in a stacked raster plot. Power from only one frequency band is shown
4) Single plot: Displays the event-related spectrogram of the most recent single event trial.
5) Continual plot: Displays the mean z-score of the last 20 ms of data from a specified frequency.

All event windows were taken from 500 ms prior to the onset of the event, and 500 ms after the onset. The z-score measurements were presented using either a normalized color scale, or a normalized gray scale.

To remove common artifact data, an algorithm was implemented for removing trials from occasionally corrupted noisy data caused by faulty electrodes in the average plot and single-trial raster. A window of data for a particular frequency band was deemed an artifact if more than 50% of the event window was below 1.5 baseline standard deviations or if more than 80% was above 1.5 baseline standard deviations. These data were displayed with a solid band of gray (or green, when in color scale) on the plot itself.

Results

Figure 11:
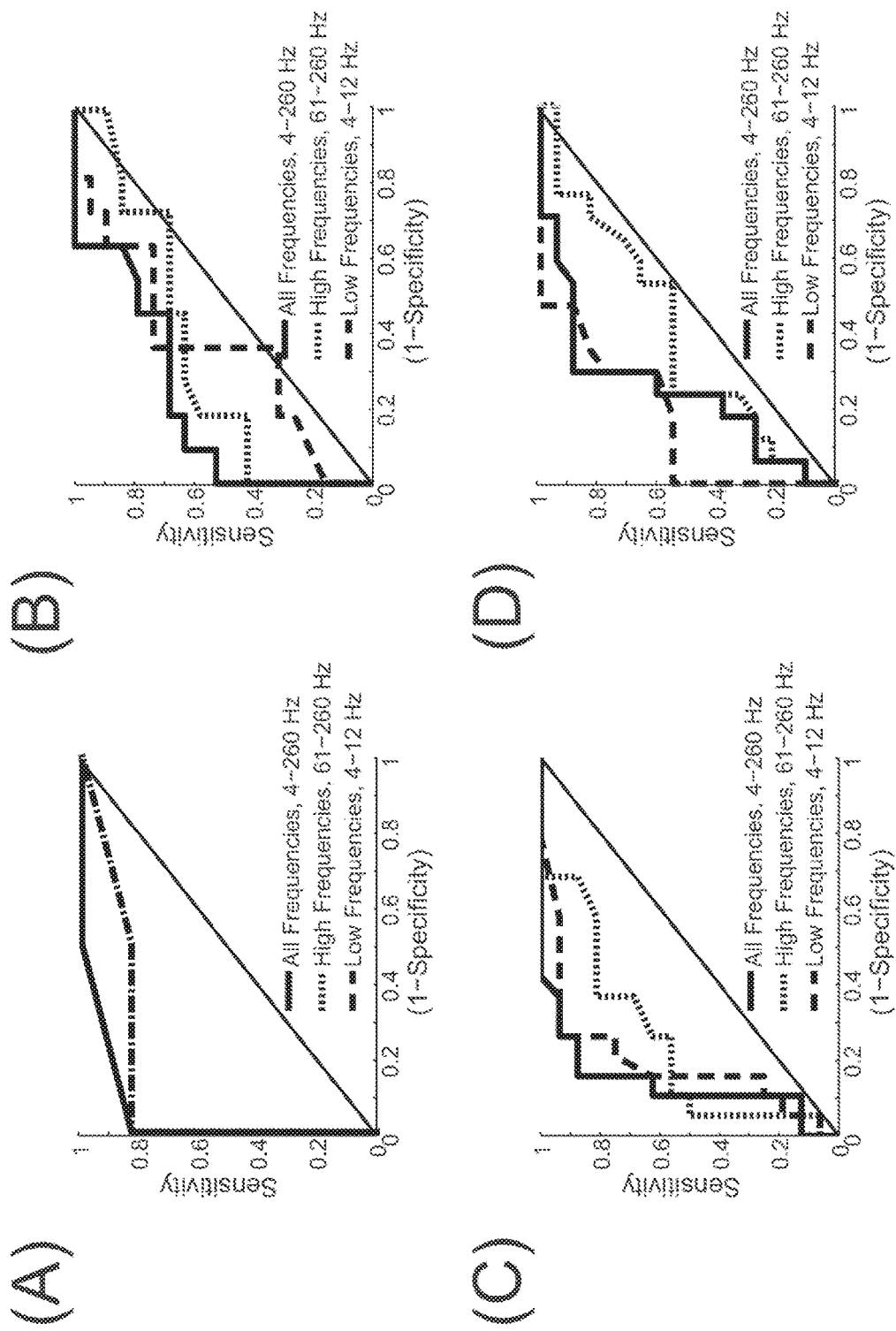
FIG. 11, Panels A-D are plots showing sensitivities and specificities for subjects. Panels A, B, C, and D are ROC plots for Subjects A, B, C, and D, respectively. Plotting conventions are the same as FIG. 8, Panel B.

It was first demonstrated that the method can be used to detect electrode-specific event-related spectral alterations. In the following presentation of data, neural activity is represented as z-score deviations from the baseline signal (depicted by a gray scale). The event onset is denoted by a vertical dotted line and labeled to be at time 0. Each plot portrays 64 channels from the entire 8×8 subdural array. Analysis of the single plot and continual plot is shown in FIG. 11, Panels A-C.

Average Plot

Figure 9:
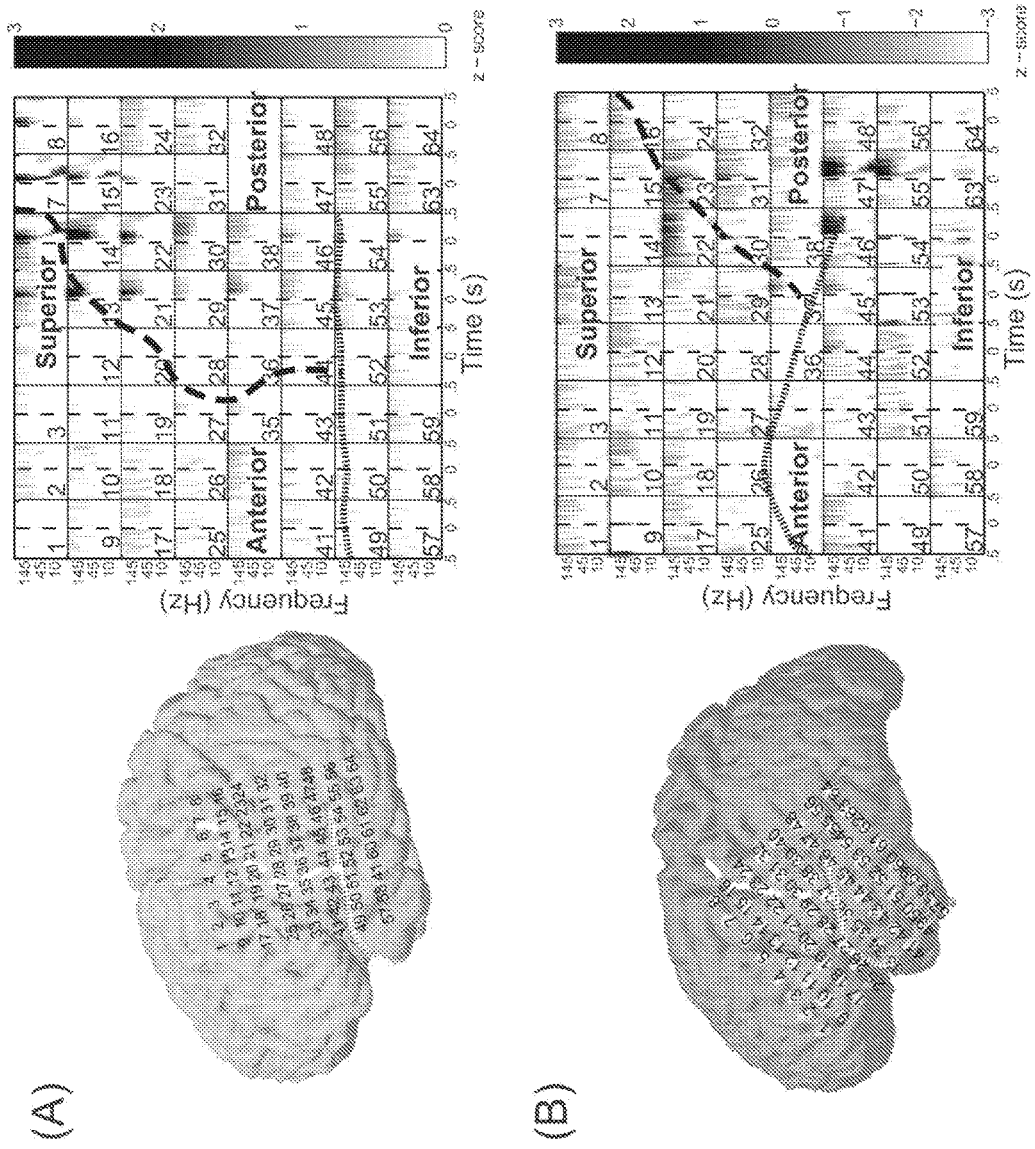
FIG. 9, Panels A-C depict average event-related spectrograms. Plots are shown depicting average event-related spectrograms for Subjects B, C, and D. Plotting conventions are the same as FIG. 2. Panel A: The average plot for Subject B was generated after the experimenter pressed the button press device against the subject's finger while the subject was resting for approximately 1 minute (Task 4). Panel B: The average plot for Subject C was generated after the subject listened to the syllable /ba/ for approximately 1 minute (Task 2). Panel C: The average plot for Subject D was generated after the subject produced the syllable /ba/ for approximately 1 minute (Task 1).
Figure 9:
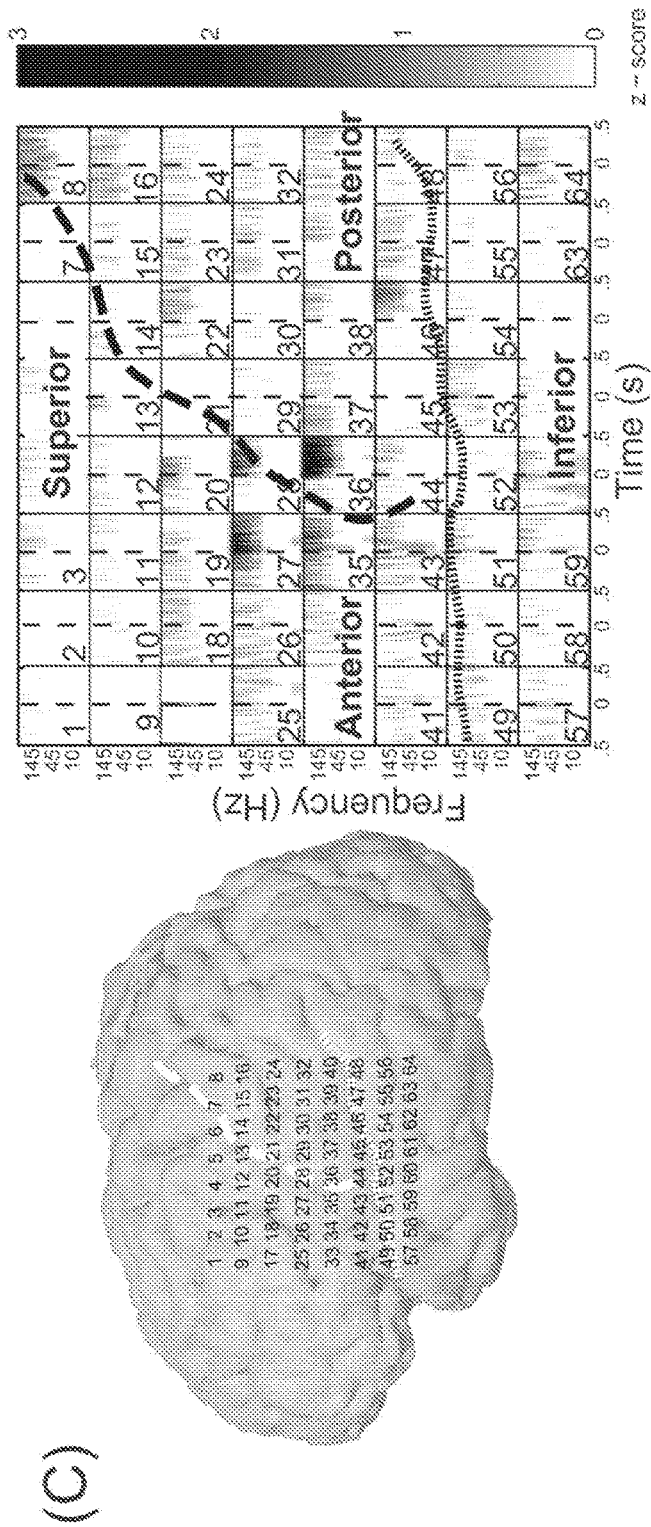

The average plot shows the running average event-related spectrogram which is updated after each event trial. Two average plots from subject A for speaking and hand movement tasks are shown in FIG. 4. Additional plots are shown in FIG. 9, Panels A-C. It can be seen which electrodes are active immediately before and after the event onset.

In FIG. 4, the average plot is shown for when the subject was instructed to produce the syllable /la/. Electrodes 15, 29, and 30 in the ventral motor strip show strong activation that are clearly event-locked, and begins slightly before event onset (−118 ms), suggesting the motor planning for the articulation. It can be seen that electrode 54 in the posterior superior temporal gyms also reveals an increase in activity, however this only occurs after event onset (72 ms), and therefore is related to auditory sensory processing.

Single-Trial Raster Plot

The raster plot displays cumulative single trials spectral changes for a given frequency range (here it is 111-179 Hz) measured in z-score deviations from the baseline. The stacked single trial plot is generated simultaneously with the same speech production task (/la/), and is shown in FIG. 5. For each new event the plot is updated with the single event trial added as a horizontal row.

The patterns observed across events demonstrate the robustness of the physiologic approach in single trials, and adds another visualization that does not require averaging which can be susceptible to outlier values. Key channels from the stacked plot can be more carefully examined on the right. Note the time axis has been extended to show a full second after the event. Again, these plots demonstrate that activity occurs earlier in the motor electrodes compared to the sensory auditory channels.

Single Plot

In the single plot, the most recent event spectrogram is shown. FIG. 10, Panel A shows one such plot from the subject's /la/ task. High event-locked z-scores can be seen, especially in channel 29. In offline analyses the maximum z-score in channel 29's single-event spectrogram was found to be significant (z-score=5.44, p-value<$2.6\times10^{-8}$, alpha-level<0.0001, 181-260 Hz, t=44 ms). While this significant activation in channel 29 corresponds well with observations made with the average and single-trial raster plots, a broad range of activations throughout the grid (darker gray to black coloring) makes it difficult to visually identify other crucial channels with the single-event spectrograms.

Continual Plot

Average z-scores of the most recent 20 ms from the grid in the 111-179 Hz band are displayed and refreshed with every iteration in the continual plot, as described in Methods. Two such plots from the subject's production of /la/ task are shown below. FIG. 10, Panel B was captured during a period of rest and shows nearly all electrodes to have insignificant z-scores (range: |z|<1.5, p-value=0.87, alpha-level<0.05). FIG. 10, Panel C was produced during an event and shows a high change from baseline in channels 29 and 54. These channels correspond to those identified in the average plots (FIG. 4). However, channels 15 and 30, seen activated in the average plot, do not show similar changes.

Robustness of the Running Average Visualization

Figure 8:
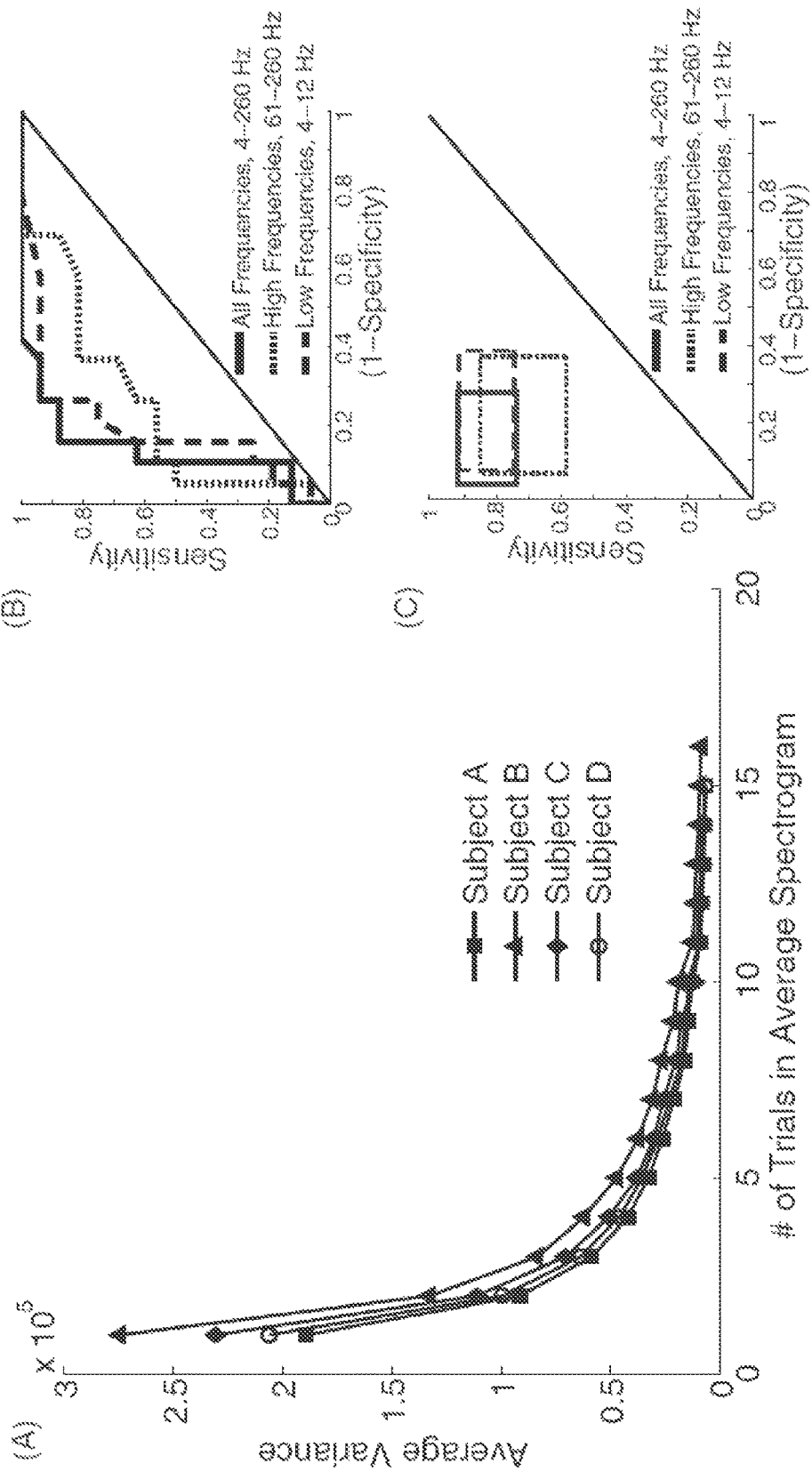
FIG. 8, Panels A-C show average variance and sensitivities and specificities for subjects. Panel A: The average variance of average plots shown as a function of the number of trials incorporated into the average. Panel B: Subject C's ROC curve. Electrode channels were categorized as positive or negative using average squared z-scores and compared against ECS maps. Z-scores from the average spectrogram after the 10th trial were used. Three spectral ranges were examined (4-260 Hz, 61-260 Hz, and 4-12 Hz). The ROC curve plots the rate of true positives (sensitivity) against the false positive rate (1-specificity). The diagonal line (line of no-discrimination) divides the ROC space between good and poor classification results. Values in the upmost left corner indicate perfect classification. Panel C: Sensitivities and specificities ranges (95% confidence intervals) were found using subject-specific optimal thresholds and plotted in the ROC space.

To examine the robustness of the algorithm, the variance of running average spectrograms was analyzed offline. All N trials within an experiment were randomized and binned to contain n number of trials in each bin (n ranging from 2 through N/2). An average spectrogram was then created from each bin of trials and a mean and variance between these spectrograms were calculated. It is important to note that no one trial is used in more than one average spectrogram, thus no bias is created. This was repeated 100 times and the average variance was calculated as a function of number of trials (FIG. 8, Panel A). A sharp exponential decay exists and the variance between average spectrograms becomes minimal after incorporating approximately 5 trials in the average, and virtually negligible after 10 events. This suggests that a very stable representation of cortical activity is achieved with very few repetitions.

Example 2: Correlation Between Real-Time Cortical Mapping and ECS Mapping

ECS mapping was performed on subjects A-D according to clinical routine in 2-3 hour blocks over 1-2 days. These procedures utilized constant current electrical stimulation between pairs of adjacent electrodes using a Grass S-88 cortical stimulator (Grass-Telefactor, West Warwick, R.I., USA). Trains of 1-5 seconds, 50 Hz, 0.3 ms, alternating polarity square-wave pulses were sent through the stimulator starting with an intensity of 1 mA. The intensity was increased at 1 mA increments, up to a maximum of 15 mA. Intensities were adjusted so that after-discharges were not produced. Patients reported any unusual or involuntary sensations or movements. Disruption of motor function was detected by observing patients during voluntary movements.

The sensitivity and specificity of the mapping algorithm were calculated for overlapping sites for which ECS was also used for clinical mapping. Sites below the Sylvian fissure were discarded since the tasks and ECS results targeted primarily the motor and somatosensory cortex that are usually mapped with ECS. Three sets of data were used: the average spectrogram z-scores after the first 10 trials for (i) all frequencies (4-260 Hz) (ii) the low frequencies (4-12 Hz), and (iii) the high frequencies (61-260 Hz). Sites were deemed positive (+) if the average squared z-score exceeded some threshold ranging from 2 to 0 with 0.01 increments, and deemed negative (−) otherwise. ECS sites were categorized by neurologists as (+) if stimulation produced unusual or involuntary sensations or movements during clinical motor mapping, and (−) otherwise. Though adjacent electrodes were stimulated together, each site was counted separately so that the two mapping techniques could be compared.

A receiver operating characteristic (ROC) curve and the area under the ROC curve (AUC) were calculated using ECS results as the correct classification. Subject C's ROC is shown in FIG. 8, Panel B.

A receiver operating characteristic (ROC) curve and the area-under-the-ROC-curve (AUC) were calculated using ECS results as the correct classification. Subject-specific ROCs are shown in FIG. 8, Panel B and in FIG. 11, Panels A-D. Averaging across patients, AUC confidence intervals were found for the three sets of data. Using all frequencies, the AUC was 0.85±0.083 (95% confidence interval). High frequency data yielded an AUC range of 0.73±0.11 (95% confidence interval). Using low frequencies, the AUC range was 0.79±0.10 (95% confidence interval). To verify that analyses were not biased from using only one baseline per day of experimentation, data was reanalyzed offline by renormalizing the data from each experimental session with its own baseline. These results were not significantly different, and suggest that only one baseline collection is necessary per day of experimentation.

The optimal threshold—defined as the threshold that yielded the sensitivity and specificity coordinate pair closest to 100% classification accuracy on the ROC curve—varied across subjects. With high frequency data, and using the subject-specific optimal threshold, the sensitivity was 70.8±13.4% (95% confidence interval) relative to ECS (+) sites. The specificity was 78.1±15.3% (95% confidence interval) relative to ECS (−) sites. For the low frequencies, the sensitivity was 82.1±8.5% (95% confidence interval) and the specificity was 77.0±15.6% (95% confidence interval). Using all frequencies, the sensitivity was 82.0±9.2% (95% confidence interval) and the specificity was 84.2±11.9% (95% confidence interval). These intervals are depicted in FIG. 8, Panel C. Again, data using baselines from the same experimental session were not significantly different.

Example 3: Median Nerve Stimulation

Due to the high-density electrode configuration of subject E, standard ECS mapping was not carried out. However, standard localization of the central sulcus using the phase reversal of somatosensory evoked potential (N20-P20) was performed. The contralateral median nerve was stimulated at the wrist with 5.1 pulses s-1 and a current intensity between 5 and 10 mA until twitches of the thumb were observed visually. The anode was placed just proximal to the palmar crease, and the cathode was placed between the tendons of the palmaris longus muscle, 3 cm proximal to the anode. ECoG signals were recorded simultaneously. The raw time series was averaged over 187 trials.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for generating an event-based visual map of functional organization of a subject's cortex in real-time, the method comprising:
    (a) receiving in real-time:
        (i) signals indicating onset of an event experienced or performed by a subject, and
        (ii) a plurality of electrocorticography (ECoG) signals before and during the event from electrodes positioned to detect the subject's brain activity;
    (b) performing real-time processing, in absence of averaging based on time, of:
        (i) the plurality of ECoG signals from the electrodes before the event to provide activation signals from motor cortex of the subject, and
        (ii) the plurality of ECoG signals from the electrodes during the event to provide activation signals from sensory cortex of the subject; and
    (c) generating a visual map of the subject's cortex delineating regions in sensory and motor cortices of the subject's brain active before and during the event based on the motor cortex and sensory cortex activation signals generated in step (b).

2. The method of claim 1, wherein generating the visual map comprises communicating the motor cortex and sensory cortex activation signals to an output device.

3. The method of claim 2, wherein the output device is a display device.

4. The method of claim 2, further comprising approximating an envelope of the plurality of ECoG signals from the electrodes, wherein the approximating an envelope is performed prior to communicating the processed motor cortex and sensory cortex signals to an output device.

5. The method of claim 4, wherein the approximating comprises applying a Hilbert transform.

6. The method of claim 4, wherein the approximating comprises applying a Fourier transform.

7. The method of claim 1, wherein the processing comprises applying a notch filter.

8. The method of claim 7, wherein the notch filter is applied at a frequency selected from 60 Hz, 120 Hz, and 180 Hz.

9. The method of claim 1, wherein the processing comprises applying a plurality of bandpass filters.

10. The method of claim 9, wherein the bandpass filters separate the signal into 2 to 8 different frequency bands.

11. The method of claim 10, wherein the bandpass filters separate the signal into 7 different frequency bands.

12. The method of claim 11, wherein the 7 different frequency bands comprise: 4 to 7 Hz, 8 to 12 Hz, 13 to 30 Hz, 31 to 59 Hz, 61 to 110 Hz, 111 to 179 Hz, and 181 to 260 Hz.

13. The method of claim 1, wherein the processing comprises applying a low-pass filter.

14. The method of claim 1, wherein the ECoG signals are sampled from the subject using microelectrodes.

15. The method of claim 1, wherein the electrodes are arranged in a grid pattern.

16. The method of claim 15, wherein the grid spacing is 0.5 cm to 1.5 cm.

17. The method of claim 1, wherein the plurality of ECoG signals from the electrodes comprise frequencies of 4 to 260 Hz.

18. The method of claim 1, wherein the plurality of ECoG signals from the electrodes comprise frequencies of 61 to 260 Hz.

19. The method of claim 1, wherein the plurality of ECoG signals from the electrodes comprise mu, beta, and gamma frequencies.

20. The method of claim 1, wherein the plurality of ECoG signals from the electrodes comprise gamma frequencies.

21. The method of claim 1, wherein the plurality of ECoG signals from the electrodes comprise high gamma frequencies.

22. The method of claim 1, further comprising positioning a plurality of ECoG electrodes to detect the subject's brain activity.

23. The method of claim 1, wherein the plurality of ECoG signals from the electrodes are recorded for a time period of at least 0.5 sec prior to onset of the event.

24. The method of claim 1, wherein the plurality of ECoG signals from the electrodes are recorded for a time period of at least 0.5 sec after onset of the event.

25. The method of claim 1, wherein the event experienced by the subject comprises listening to a verbal sound.

26. The method of claim 25, wherein the verbal sound comprises a syllable sound.

27. The method of claim 1, wherein the event performed by a subject comprises making a verbal sound.

28. The method of claim 27, wherein the verbal sound comprises a syllable sound.

29. The method of claim 1, wherein the event experienced by the subject comprises a button press device being pressed against the subject's finger.

30. The method of claim 1, wherein the event performed by the subject comprises pressing a button using a thumb.

31. A cortical mapping system configured to generate an event-based visual map of functional organization of a subject's cortex, the system comprising:
    a plurality of electrodes configured to detect a subject's brain activity;
    a processor; and
    memory operably coupled to the processor, wherein the memory includes instructions stored thereon that, when executed by the processor, cause the processor to perform real-time operations comprising:
    (a) receiving in real-time:
        (i) signals indicating onset of an event experienced or performed by the subject, and
        (ii) a plurality of electrocorticography (ECoG) signals before and during the event from electrodes positioned to detect the subject's brain activity;
    (b) performing real-time processing, in absence of averaging based on time, of:
        (i) the plurality of ECoG signals from the electrodes before the event to provide activation signals from motor cortex of the subject, and
        (ii) the plurality of ECoG signals from the electrodes during the event to provide activation signals from sensory cortex of the subject; and
    (c) generating a visual map of the subject's cortex delineating regions in sensory and motor cortices of the subject's brain active before and during the event based on the motor cortex and sensory cortex activation signals generated in step (b).

* * * * *

UNITED STATES PATENT AND TRADEMARK OFFICE
CERTIFICATE OF CORRECTION

PATENT NO. : 10,492,702 B2
APPLICATION NO. : 14/375099
DATED : December 3, 2019
INVENTOR(S) : Edward F. Chang et al.

Page 1 of 1

It is certified that error appears in the above-identified patent and that said Letters Patent is hereby corrected as shown below:

In the Specification

In Column 10, Line 62, please change "gyms" to --gyrums--;

In Column 13, Line 5, please change "gyms" to --gyrums--;

In Column 24, Line 17, please change "gyms" to --gyrums--.

Signed and Sealed this
Thirtieth Day of June, 2020

Andrei Iancu
*Director of the United States Patent and Trademark Office*